United States Patent
Jewett et al.

(10) Patent No.: US 9,458,143 B1
(45) Date of Patent: Oct. 4, 2016

(54) TRIAZABUTADIENES AS ADDITIVES IN ADHESIVE SYSTEMS

(71) Applicant: THE ARIZONA BOARD OF REGENTS ON BEHALF OF THE UNIVERSITY OF ARIZONA, Tucson, AZ (US)

(72) Inventors: John C. Jewett, Tucson, AZ (US); Flora W. Kimani, Tucson, AZ (US)

(73) Assignee: THE ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 14/918,287

(22) Filed: Oct. 20, 2015

Related U.S. Application Data

(63) Continuation-in-part of application No. PCT/US2015/035136, filed on Jun. 10, 2015.

(60) Provisional application No. 62/128,707, filed on Mar. 5, 2015, provisional application No. 62/114,735, filed on Feb. 11, 2015, provisional application No. 62/109,170, filed on Jan. 29, 2015, provisional application No. 62/010,861, filed on Jun. 11, 2014.

(51) Int. Cl.

| | |
|---|---|
| C08G 59/00 | (2006.01) |
| C07D 405/12 | (2006.01) |
| C07D 233/88 | (2006.01) |
| C07D 277/50 | (2006.01) |
| C07D 235/30 | (2006.01) |

(Continued)

(52) U.S. Cl.
CPC .......... *C07D 405/12* (2013.01); *C07D 233/88* (2013.01); *C07D 235/30* (2013.01); *C07D 277/50* (2013.01); *C07D 277/82* (2013.01); *C09J 163/00* (2013.01)

(58) Field of Classification Search
CPC .......... C08G 73/08; C08G 2261/3221; C08G 12/28; A61K 47/48; A61K 31/5575
See application file for complete search history.

(56) References Cited

U.S. PATENT DOCUMENTS

| | | |
|---|---|---|
| 3,591,575 A | 7/1971 | Golda |
| 3,607,542 A | 9/1971 | Brandes et al. |

(Continued)

FOREIGN PATENT DOCUMENTS

| | | |
|---|---|---|
| DE | 265008 A1 | 2/1989 |
| DE | 4242428 A1 | 10/1993 |

(Continued)

OTHER PUBLICATIONS

Kimani and Jewett, 2015, Angewandte Chemie International Edition (DOI: 10.1002/anie201411277—Online ahead of print).

(Continued)

*Primary Examiner* — Shane Fang

(57) ABSTRACT

Triazabutadiene molecules that provide adhesive functionality, e.g., triazabutadiene molecules as underwater adhesives or water-reactive adhesives. The triazabutadiene molecules mask an aryl diazonium ion, a highly reactive chemical functionality. Once unmasked, e.g., in water, the diazonium species is adapted to react with an electron rich aryl ring that can undergo diazonium chemistry (e.g., phenol species, resorcinol species, etc.). Triazabutadienes can be used as additives in adhesive systems such as but not limited to epoxy adhesive systems.

13 Claims, 18 Drawing Sheets

(51) Int. Cl.
*C07D 277/82* (2006.01)
*C09J 163/00* (2006.01)

(56) References Cited

U.S. PATENT DOCUMENTS

| | | | |
|---|---|---|---|
| 3,959,210 | A | 5/1976 | Lipatova et al. |
| 4,107,353 | A | 8/1978 | Karoly et al. |
| 4,218,279 | A | 8/1980 | Green |
| 4,356,050 | A | 10/1982 | Crivello et al. |
| 4,602,073 | A | 7/1986 | Skoultchi et al. |
| 5,856,373 | A | 1/1999 | Kaisaki et al. |
| 8,603,451 | B2 | 12/2013 | Zhang et al. |
| 8,617,827 | B2 | 12/2013 | Hell et al. |
| 2002/0197439 | A1 | 12/2002 | Berneth et al. |
| 2004/0241205 | A1 | 12/2004 | Babich et al. |
| 2005/0080260 | A1 | 4/2005 | Mills et al. |
| 2007/0049587 | A1 | 3/2007 | Zbinden et al. |
| 2007/0098807 | A1 | 5/2007 | Babich et al. |
| 2007/0104719 | A1 | 5/2007 | Carter et al. |
| 2009/0048222 | A1 | 2/2009 | Bell et al. |
| 2009/0286308 | A1 | 11/2009 | Berthelot et al. |
| 2011/0245287 | A1 | 10/2011 | Holaday et al. |

FOREIGN PATENT DOCUMENTS

| | | | |
|---|---|---|---|
| WO | WO 2008/090554 | A2 | 7/2008 |
| WO | WO 2009/137916 | A1 | 11/2009 |

OTHER PUBLICATIONS

Zhong et al., 2014, Nature Nanotechnology 9, 858-866.
Stewart et al., 2011, J Polym Sci B Polym Phys 49(11):757-771.
Poulsen et al., 2014, Biofouling 30(4):513-23.
Stewart, 2011, Appl Microbiol Biotechnol 89(1):27-33.
Stewart et al., 2011, Adv Colloid Interface Sci 167(1-2):85-93.
Hennebert et al., 2015, Interface Focus 5(1):2014.
Y. Modis, S. Ogata, D. Clements, S. C. Harrison, Nature 2004, 427, 313-319.
C. D. Blanchette, Y. H. Woo, C. Thomas, N. Shen, T. A. Sulchek, A. L. Hiddessen, PLoS One 2009, 4, e6056.
J. Han, K. Burgess, Chem. Rev. 2010, 110, 2709-2728.
J. Kalia, R. T. Raines, Angew. Chem. Int. Ed. Engl. 2008, 47, 7523-7526.
J. Kalia, R. T. Raines, Angew. Chem. 2008, 120, 7633-7636.
J. Z. Du, X. J. Du, C. Q. Mao, J. Wang, J. Am. Chem. Soc. 2011, 133, 17560-17563.
E. H. Cordes, H. G. Bull, Chem. Rev. 1974, 74, 581-603.
A. Luong, T. Issarapanichkit, S. D. Kong, R. Fonga, J. Yang, Org. Biomol. Chem. 2010, 8, 5105-5109.
Fanghänel, R. Hänsel, W. Ortmann, J. Hohlfeld, J. Prakt. Chem. 1975, 317, 631-640.
H.-T. Dorsch, H. Hoffmann, R. Hansel, G. Rasch, E. Fanghänel, J. Prakt. Chem. 1976, 318, 671-680.
E. Fanghänel, R. Hänsel, J. Hohlfeld, J. Prakt. Chem. 1977, 319, 485-493.
E. Fanghänel, H. Poleschner, R. Radeglia, R. Hänsel, J. Prakt. Chem. 1977, 319, 813-826.
E. Fanghänel, J. Hohlfeld, J. Prakt. Chem. 1981, 323, 253-261.
R. Radeglia, R. Wolff, T. Steiger, S. Simova, E. Fanghanel, J. Prakt. Chem. 1984, 5, 511-514.
E. Fanghänel, W. Ortmann, A. Hennig, J. Prakt. Chem. 1988, 330, 27-34.
E. Fanghänel, W. Ortmann, J. Prakt. Chem. 1989, 331, 721-725.
E. Fanghänel, J. U. Bauroth, H. Hentschel, F. Gußmann, H. Alzyadi, W. Ortmann, J. Prakt. Chem. 1992, 334, 241-247.
D. M. Khramov, C. W. Bielawski, Chem. Commun. 2005, 4958-4960.
S. Dahmen, S. Brase, Org. Lett. 2000, 2, 3563-3565.
S. Brase, Acc. Chem. Res. 2004, 37, 805-816.
D. Jishkariani, C. D. Hall, A. Demircan, B. J. Tomlin, P. J. Steel, A. R. Katritzky, J. Org. Chem. 2013, 78, 3349-3354.
D. M. Khramov, C. W. Bielawski, J. Org. Chem. 2007, 72, 9407-9417.
A. G. Tennyson, E. J. Moorhead, B. L. Madison, J. A. V. Er, V. M. Lynch, C. W. Bielawski, Eur. J. Org. Chem. 2010, 6277-6282.
W. Herrmann, C. Köcher, Angew. Chem. Int. Ed. 1997, 36, 2162-2187.
W. Herrmann, C. Köcher, Angew. Chem. 1997, 109, 2256-2282.
N. Marion, S. Díez-González, S. P. Nolan, Angew. Chem. Int. Ed. Engl. 2007, 46, 2988-3000.
N. Marion, S. Díez-González, S. P. Nolan, Angew. Chem. 2007, 119, 3046-3058.
A. F. Hegarty, in The Chemistry of Diazonium and Diazo Groups, vol. 2 (Ed.: S. Patai), John Wiley & Sons, Ltd., New York, NY, 1978, pp. 511-591.
L. P. Hammett, J. Am. Chem. Soc. 1937, 59, 96-103.
B. M. Tracey, D. E. G. Shuker, Chem. Res. Toxicol. 1997, 10, 1378-1386.
J. M. Hooker, E W. Kovacs, M. B. Francis, J. Am. Chem. Soc. 2004, 126, 3718-3719.
J. Gavrilyuk, H. Ban, M. Nagano, W. Hakamata, C. F. Barbas III, Bioconjugate Chem. 2012, 23, 2321-2328.
L. Wang, V. Gruzdys, N. Pang, F. Meng, X.-L. Sun, RSC Adv. 2014, 4, 39446.
European Journal of Inorganic Chemistry vol. 2013, Issue 12, p. 2020-2030, Apr. 2013 Elena Garcia-Moreno, Elena Cerrada, M. José Bolsa, Asunción Luquin and Mariano Laguna.
European Journal of Medicinal Chemistry vol. 46, Issue 7, Jul. 2012, p. 2748-2758, Marijana Hranjeca, Borka Lučića, Ivana Ratkajb, Sandra Kraljević Pavelićb, Ivo Piantanidac, Krešimir Pavelićb, Grace Karminski-Zamola.
Flora Kimani and John Jewett, DOI: 10.1002/anie.201411277 Water-Soluble Triazabutadienes that Release Diazonium Species upon Protonation under Physiologically Relevant Conditions.
Chao Zhong, Thomas Gurry, Allen A. Cheng, Jordan Downey, Zhengtao Deng, Collin M. Stultz, Timothy K. Lu, Nature Nanotechnology 9, 858-866 (2014).
Stewart RJ, Ransom TC, Hlady V, J Polym Sci B Polym Phys. Jun. 2011;49(11):757-771.
Poulsen N, Kröger N, Harrington MJ, Brunner E, Paasch S, Buhmann MT, Biofouling. 2014;30(4):513-23.
Stewart RJ, Appl Microbiol Biotechnol. Jan. 2011;89(1):27-33.
Stewart RJ, Wang CS, Shao H, Adv Colloid Interface Sci. Sep. 14, 2011;167(1-2):85-93.
Hennebert E, Maldonado B, Ladurner P, Flammang P, Santos R, Interface Focus. Feb. 6, 2015;5(1):2014.

| Formula I |  |
|---|---|
| Formula II |  |
| Formula III |  |
| Formula IV |  |

*Figure 6F*
*Figure 6G*
*Figure 6H*
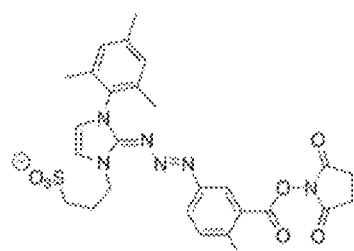
Readily synthesized from an
N-heterocyclic carbene and a
commercially available NHS-azide.
*Figure 6I*
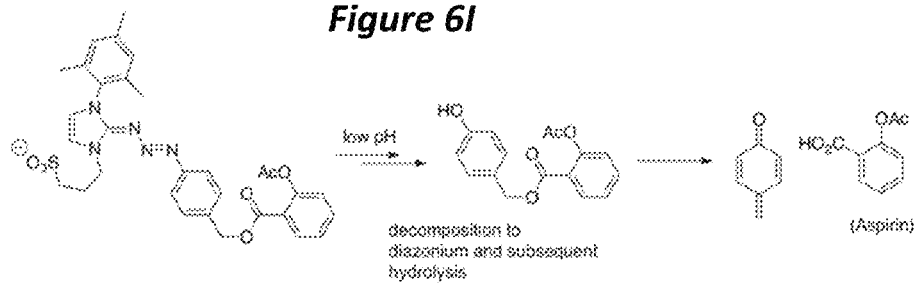
*Figure 6J*
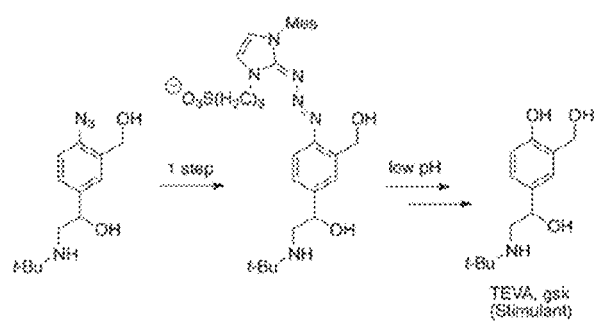

TRIAZABUTADIENES AS ADDITIVES IN ADHESIVE SYSTEMS

CROSS REFERENCE

This application is a continuation in part of PCT/US15/35136 filed on Jun. 10, 2015, which claims priority to U.S. Provisional Application No. 62/010,861, filed Jun. 11, 2014, U.S. Provisional Application No. 62/109,170 filed Jan. 29, 2015, U.S. Provisional Application No. 62/114,735 filed Feb. 11, 2015, and U.S. Provisional Application No. 62/128,707 filed Mar. 5, 2015, the specifications of which are incorporated herein in their entirety by reference.

BACKGROUND OF THE INVENTION

The present invention features triazabutadiene molecules that provide adhesive functionality, e.g., triazabutadiene molecules as underwater adhesives or water-reactive adhesives. These triazabutadiene molecules mask an aryl diazonium ion, a highly reactive chemical functionality. Once unmasked, the diazonium species is adapted to react with an electron rich aryl ring that can undergo diazonium chemistry (e.g., phenol species, resorcinol species, etc.). Triazenes have previously been used to make an aryl diazonium species, but a strong acid was required (see Kimball, D. B. and Haley, M. M. (2002), Triazenes: A Versatile Tool in Organic Synthesis. Angew. Chem. Int. Ed., 41: 3338-3351). The use of strong acids may not necessarily be practical for particular applications. The triazabutadienes of the present invention can unmask the aryl diazonium species in water (or other conditions as described herein).

Inventors have surprisingly discovered that triazabutadienes can be used as additives in adhesive systems. For example, the present invention features triazabutadiene molecules that can be incorporated into epoxy adhesives. For example, a series of surprising orthogonal reactions featuring triazabutadienes and epoxy chemistry (as shown in FIG. 10A) provides for a new adhesive composition.

SUMMARY

The present invention features triazabutadiene molecules as adhesives and 1. triazabutadiene molecules as additives in adhesive systems. For example, the present invention features a triazabutadiene molecule according to formula 1 below.

In some embodiments, A=S, O, or N; D=H, —CH=CH—CH=E-, halides, cyano, sulfonates, alkyl chain, or trifluoromethyl. In some embodiments, E=H, —CH=CH—CH=D-, halides, cyano, sulfonates, alkyl chain, or trifluoromethyl. In some embodiments, $X^1$=—$R^1$—$Q^1$; wherein —$R^1$=alkanes and $Q^1$=sulfonate, phosphate, or a quaternary ammonium cation, or an alkyl, aryl or propargylic containing moiety that can facilitate coupling to other azides via [3+2]cycloaddition chemistry. In some embodiments, $Y^1$=tri-substituted aryl group or alkyl substituents. In some embodiments, $Z^1$=polymerization residue.

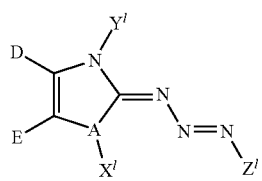

In some embodiments, $R^1$ of $X^1$ comprises C1-6 alkylenes. In some embodiments, the tri-substituted aryl group of $Y^1$ comprises a NHS-ester moiety; an oligonucleotide; a peptide; a fluorescence quencher; a pro-fluorophore; an alkyne or a triazene. In some embodiments, the polymerization residue of $Z^1$ comprises an epoxide. In some embodiments, the polymerization residue comprises polystyrene, α-β-unsaturated ester acrylate, polyacrylamide, or an amine.

The present invention also features formulations comprising a triazabutadiene molecule and an epoxide resin. In some embodiments, the triazabutadiene molecule is according to Formula 1 as described above. For example, in some embodiments, A=S, O, or N; D=H, —CH=CH—CH=E-, halides, cyano, sulfonates, alkyl chain, or trifluoromethyl. In some embodiments, E=H, —CH=CH—CH=D-, halides, cyano, sulfonates, alkyl chain, or trifluoromethyl. In some embodiments, $X^1$=—$R^1$-$Q^1$; wherein —$R^1$=alkanes and $Q^1$=sulfonate, phosphate, or a quaternary ammonium cation, or an alkyl, aryl or propargylic containing moiety that can facilitate coupling to other azides via [3+2]cycloaddition chemistry. In some embodiments, $Y^1$=tri-substituted aryl group or alkyl substituents. In some embodiments, $Z^1$=polymerization residue.

In some embodiments, the epoxide resin comprises an aliphatic epoxide, e.g., a molecule according to the structure:

In some embodiments, n=1-10. In some embodiments, n=1, 2, 3, 4, 5, 6, 7, 8, 9, or 10. In some embodiments, n=greater than 10. In some embodiments, the epoxide resin comprises an electron rich aryl compound, e.g., a molecule according to the structure:

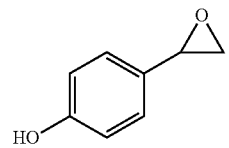

The present invention also features methods of producing adhesives. In some embodiments, the method comprises providing a composition A. In some embodiments, composition A comprises:

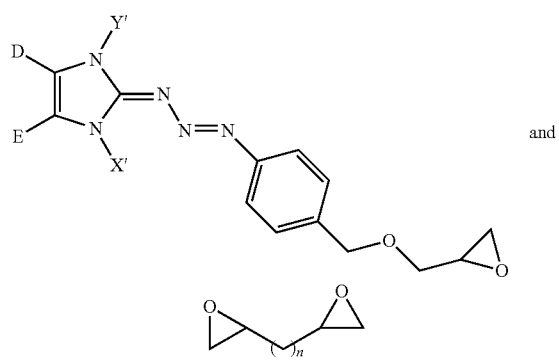

and or

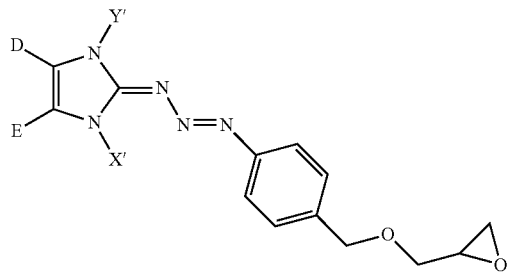

and

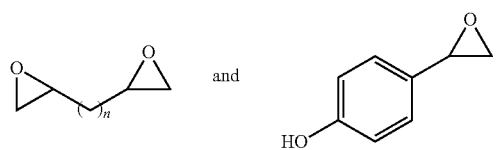

In some embodiments, A=S, O, or N; D=H, —CH=CH—CH=E-, halides, cyano, sulfonates, alkyl chain, or trifluoromethyl. In some embodiments, E=H, —CH=CH—CH=D-, halides, cyano, sulfonates, alkyl chain, or trifluoromethyl. In some embodiments, $X^l$=—$R$-$Q^1$; wherein —$R^1$=alkanes and $Q^1$=sulfonate, phosphate, or a quaternary ammonium cation, or an alkyl, aryl or propargylic containing moiety that can facilitate coupling to other azides via [3+2] cycloaddition chemistry. In some embodiments, $Y^l$=tri-substituted aryl group or alkyl substituents. In some embodiments, n=1-10. In some embodiments, n=1, 2, 3, 4, 5, 6, 7, 8, 9, or 10. In some embodiments, n=greater than 10. The method may further comprise providing a composition B. In some embodiments, composition B comprises

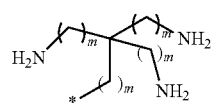

or

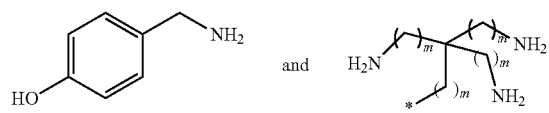

In some embodiments, m=1-5. In some embodiments, m=1, 2, 3, 4, or 5. In some embodiments, m is greater than 5. The method may further comprise mixing composition A and composition B to form a product C, product C being the adhesives. In some embodiments, product C comprises

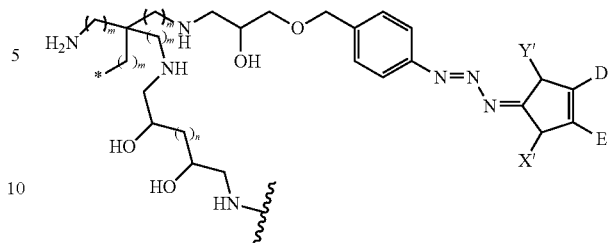

Product C above is a non-limiting example of a product of Composition A and Composition B. Product C is not limited to this structure. For example, in some embodiments, the epoxy is directly linked to the aryl ring. Note that the triazabutadiene can be attached to either the amine or epoxy side. In some embodiments, an amine is present on the triazabutadiene (in which case it could be added into the epoxy-containing monomers).

In some embodiments, A=S, O, or N; D=H, —CH=CH—CH=E-, halides, cyano, sulfonates, alkyl chain, or trifluoromethyl. In some embodiments, E=H, —CH=CH—CH=D-, halides, cyano, sulfonates, alkyl chain, or trifluoromethyl. In some embodiments, $X^l$=—$R^1$-$Q^1$; wherein —$R^1$=alkanes and $Q^1$=sulfonate, phosphate, or a quaternary ammonium cation, or an alkyl, aryl or propargylic containing moiety that can facilitate coupling to other azides via [3+2]cycloaddition chemistry. In some embodiments, $Y^l$=tri-substituted aryl group or alkyl substituents.

In some embodiments, n=1-10. In some embodiments, n=1, 2, 3, 4, 5, 6, 7, 8, 9, or 10. In some embodiments, n=greater than 10. In some embodiments, m=1-5. In some embodiments, m=1, 2, 3, 4, or 5. In some embodiments, m is greater than 5.

In some embodiments, the method further comprises exposing product C to water, whereby a diazonium species is formed from the triazabutadiene; the diazonium species can react with an electron rich aryl compound (e.g., a phenol compound).

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

FIGS. 6A, 6B, 6C, 6D, 6E, 6F, 6G, 6H, 6I, and 6J show non-limiting examples of triazabutadienes.

DESCRIPTION OF PREFERRED EMBODIMENTS

I. Triazabutadiene Molecules

The present invention features triazabutadiene molecules. Non-limiting examples of formulas for triazabutadiene molecules of the present invention are of shown in FIG. 1. The present invention is not limited to Formula I, Formula II, Formula III, and Formula IV. See also Formula 1 above.

Figure 1:
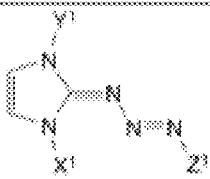
FIG. 1 shows examples of formulas of triazabutadiene molecules of the present invention.
Figure 1:
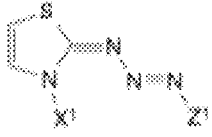
Figure 1:
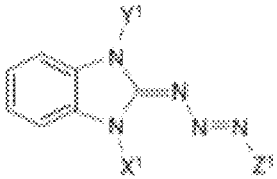
Figure 1:
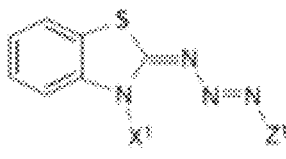

Referring to FIG. 1, in some embodiments, $X^1$ is a moiety conferring water solubility. In some embodiments, $Y^1$ is a tri-substituted aryl group. In some embodiments, the $Y^1$ (e.g., the tri-substituted aryl group) comprises a NHS-ester moiety (e.g., for protein linkage); an oligonucleotide; a peptide; a fluorescence quencher; a pro-fluorophore; an alkyne (e.g., for click chemistry); a triazene (e.g., from click reaction); the like, or a combination thereof. In some embodiments, $Y^1$ comprises an aldehyde; an amine (e.g., Fmoc protected), aminooxy, halogen (e.g., radio isotope); the like, or a combination thereof. In some embodiments, $Z^1$ is an optionally substituted aryl. In some embodiments, $Z^1$ comprises a NHS-ester moiety; an oligonucleotide; a peptide; a fluorescence quencher; a pro-fluorophore; a biologically active acid labile compound: a prodrug comprising a phenolic functional group; releasable cargo; an alkyne (e.g., for click chemistry); a triazene (e.g., from click reaction); the like, or a combination thereof. In some embodiments, $Z^1$ comprises an aldehyde; an amine (e.g., Fmoc protected), aminooxy, halogen (e.g., radio isotope); the like, or a combination thereof.

As previously discussed, $X^1$ may comprise a functional group that confers water solubility. In some embodiments, $X^1$ comprise a moiety of the formula $-R^1-Q^1$, wherein $R^1$ is $C_{1-6}$ alkylene, and $Q^1$ is sulfate, phosphate, or a quaternary ammonium cation. In some embodiments, $X^1$ is a moiety of the formula $-R^1-Q^1$, wherein $R^1$ is $C_{1-6}$ alkylene, and $Q^1$ is sulfate (e.g., $-(O)_nSO_3R^a$, where n is 0 or 1, and $R^a$ is C1-6 alkyl or typically H), phosphate (e.g., $-(O)_nPO_3R^a$ where n is 0 or 1, and $R^a$ is C1-6 alkyl or typically H), or a quaternary ammonium cation (e.g., $-[NR^aR^bR^c]^+$, where each of $R^a$, $R^b$, and $R^c$ is independently H or $C_{1-6}$ alkyl). As used herein, the term "alkyl" refers to a saturated linear monovalent hydrocarbon moiety of one to twelve, typically one to six, carbon atoms or a saturated branched monovalent hydrocarbon moiety of three to twelve, typically three to six, carbon atoms. Examples of alkyl groups include, but are not limited to, methyl, ethyl, n-propyl, 2-propyl, tert-butyl, pentyl, and the like. The term "alkylene" refers to a saturated linear divalent hydrocarbon moiety of one to twelve, typically one to six, carbon atoms or a branched saturated divalent hydrocarbon moiety of three to twelve, typically three to six, carbon atoms. Examples of alkylene groups include, but are not limited to, methylene, ethylene, propylene, butylene, pentylene, and the like.

In some embodiments, the triazabutadiene molecules of the present invention are readily soluble in water. In some embodiments, the triazabutadiene molecules of the present invention are not readily soluble in water. In some embodiments, the solubility of the triazabutadiene molecules of the present invention in water is at least 23 g/L of water (50 mM). In some embodiments, the triazabutadiene molecules of the present invention are stable in pH 7.4 phosphate buffer. The phosphate buffer solutions are commercially available or can be prepared, for example, as described in http://cshprotocols.cshlp.org/content/2006/1/pdb.rec8247.

In some instances, the half-life of the triazabutadiene molecules of the present invention in pH 7.4 phosphate buffer solution is at least 24 hours.

Stability of the triazabutadiene molecule can be measured in various ways. In some embodiments, stability is measured by the half-life of the molecule. In some embodiments, the molecule has a half-life of at least 12 hours in a pH 7.4 buffer. In some embodiments, the molecule has half-life of at least 24 hours in a pH 7.4 buffer. In some embodiments, the molecule has half-life of at least 36 hours in a pH 7.4 buffer. The present invention is not limited to the aforementioned examples of stability measurements.

Without wishing to limit the present invention to any theory or mechanism, it is believed that the triazabutadiene molecules of the present invention are advantageous because the triazabutadiene molecules can be easily modified (e.g., various different functional groups can be easily used as $X^1$, $Y^1$, or $Z^1$ (see FIG. 1). And, the release of the diazonium species following triazabutadiene molecule breakdown (via certain mechanisms, as described below) provides a functional group that can be taken advantage of in various applications. Also, it may be considered advantageous that the breakdown of the triazabutadiene molecule is irreversible.

II. Cleavage of Triazabutadiene Molecules a. Water and/or Low pH

Figure 2A:
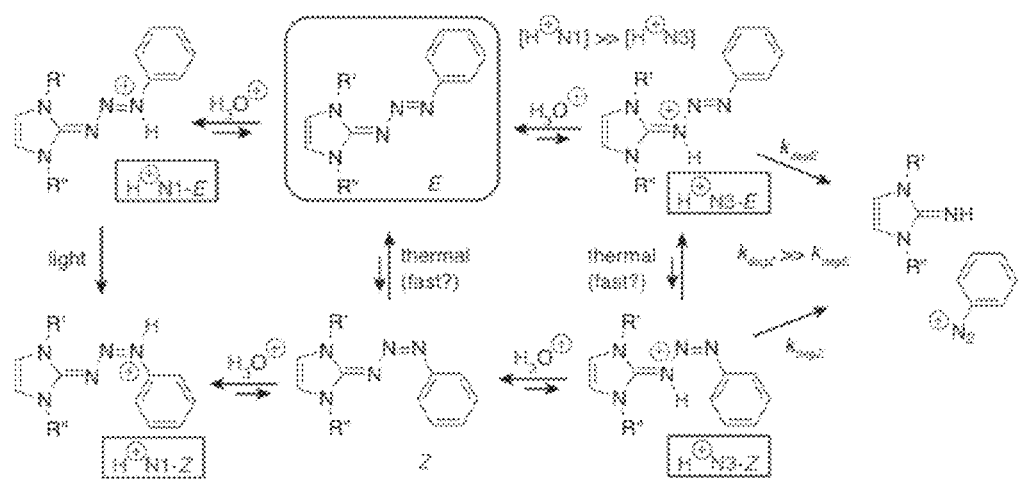
FIG. 2A shows triazabutadiene molecules undergoing decomposition to diazonium salts (and cyclic guanidine species). Note the Reaction/equilibrium arrows are not to scale.
Figure 2B:
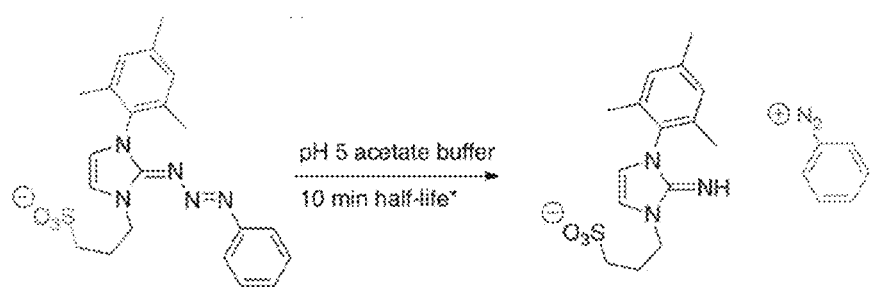
FIG. 2B shows a triazabutadiene molecule breaking down (in low pH conditions) to a diazonium species and a cyclic guanidine species.

The present invention shows that triazabutadiene molecules may break down in the presence of water to generate reactive aryl diazonium compounds. For example, FIG. 2A shows that triazabutadiene molecules of the present invention can undergo decomposition to diazonium salts (reactive aryl diazonium compounds) and cyclic guanidine species. Aryl diazonium compounds can react with electron-rich aryl rings (e.g., aryl species wherein the bond of interest is a nitrogen-carbon bond; indoles, anilines, phenol-containing compounds such as resorcinol or tyrosine, etc.) to form stable azobenzene linkages (e.g., an aryl azo dye, e.g., Sudan Orange) (e.g., see FIG. 5, top scheme). The phenol-containing species is not limited to the aforementioned examples. In some embodiments, Imidazole compounds (e.g., purine bases like guanine) may be used in lieu of a phenol-containing compound.

Figure 5:
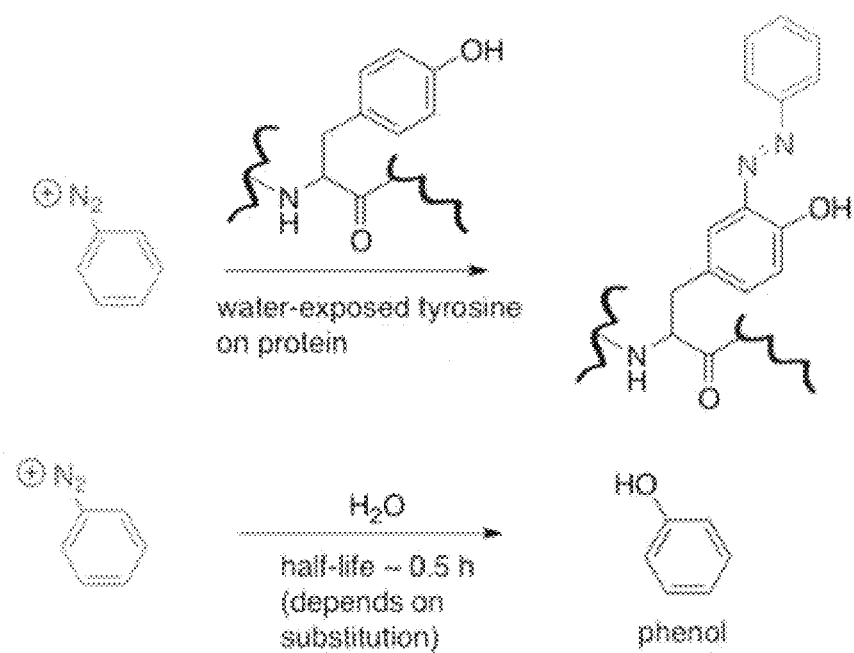
FIG. 5 shows reactions with aryl diazonium species in water. In the top scheme, the phenol-containing species is a tyrosine molecule (on a protein). In the bottom scheme, the diazonium species decomposes into a phenol species.

Referring to FIG. 5 (bottom scheme), the diazonium species, If not reacted with an electron-rich aryl ring compound (e.g., phenol species), when a phenol species is not present, may irreversibly extrude nitrogen gas to generate an aryl cation, which will rapidly be quenched by solvating water, thus synthesizing a new phenolic compound (e.g., HO-Ph, wherein Ph refers to the phenyl ring); thus, the diazonium portion of the triazabutadiene molecule may function as a masked hydroxyl group.

In some embodiments, the triazabutadiene molecules are acid labile (e.g., unstable at particular pH levels). For example, decreases in pH increase the rate at which the triazabutadiene molecules break down (the half life of the molecule decreases). In some embodiments, the triazabutadiene molecules are unstable at low (lowered) pH levels (e.g., lowered pH as compared to a particular pH that the molecule may be stored at, e.g., a pH wherein the molecule has a particular desired half life). Low pH levels, in some example, may be a sub-physiological pH (7.4 or less). In some embodiments, the triazabutadiene molecules are (more) unstable at pH 7.0 or less, pH 6.8 or less, pH 6.5 or less, pH 6.2 or less, pH 6.0 or less, pH 5.8 or less, pH 5.6 or less, pH 5.5 or less, pH 5.2 or less, pH 5.0 or less, etc. In some embodiments, the triazabutadiene molecule has a half-life of at least 8 hours. In some embodiments, the triazabutadiene molecule has a half-life of at least 10 hours. In some embodiments, the triazabutadiene molecule has a half-life of at least 12 hours. In some embodiments, the triazabutadiene molecule has a half-life of at least 20 hours. In some embodiments, the triazabutadiene molecule has a half-life of at least 24 hours. In some embodiments, the triazabutadiene molecule has a half-life of at least 30 hours. In some embodiments, the triazabutadiene molecule has a half-life of at least 36 hours.

The term 'low pH" may refer to several different pH levels. Since the functional groups attached to the molecule (e.g., see $X^1$, $Y^1$, $Z^1$ of Formula I) affect the stability of the molecule (as well as water solubility), the pH that is necessary to increase the rate of breakdown of the triazabutadiene molecule (e.g., the "lowered pH") may be different for different molecules. In some embodiments, the low pH is a pH of 7.4 or less. In some embodiments, the low pH Is a pH of 7.2 or less. In some embodiments, the low pH is a pH of 7.0 or less. In some embodiments, the low pH is a pH of 6.8 or less. In some embodiments, the low pH is a pH of 6.6 or less. In some embodiments, the low pH is a pH of 6.6 or less. In some embodiments, the low pH is a pH of 6.6 or less. In some embodiments, the low pH is a pH of 6.5 or less. In some embodiments, the low pH is a pH of 6.4 or less. In some embodiments, the low pH is a pH of 6.2 or less. In some embodiments, the low pH is a pH of 6.0 or less. In some embodiments, the low pH is a pH of 5.8 or less. In some embodiments, the low pH is a pH of 5.5 or less. In some embodiments, the low pH is a pH of 5.0 or less.

In some embodiments, the triazabutadiene molecules can break down without the presence of the low pH (the molecules have half lives); however, in some embodiments, a lowered pH enhances the reaction (e.g., increases the rate of reaction). As such, a low pH may or may not be used with the molecules and/or methods of the present invention.

The present invention also features methods of breaking down triazabutadiene molecules. In some embodiments, the method comprises subjecting the molecule to water. In some embodiments, the method comprises subjecting the molecule to a low pH (e.g., a low pH that is appropriate for the molecule, e.g., a lowered pH that increases the rate at which the triazabutadiene molecule breaks down).

In some embodiments, the diazonium species may be visually differentiated from the triazabutadiene species, e.g., the diazonium species is visually distinct (e.g., a different color) from the triazabutadiene molecule. If applicable, in some embodiments, the aryl azo dye may be visually differentiated from the triazabutadiene species and the diazonium species, e.g., the aryl azo dye is visually distinct (e.g., a different color) from the triazabutadiene species and the diazonium species.

Given the possibility that the aryl azo dye is visually distinct from the triazabutadiene molecule (and/or the diazonium species), the present invention also features methods of producing a visually detectable molecule. In some embodiments, the method comprises providing a triazabutadiene molecule according to the present invention and subjecting the triazabutadiene molecule to water and/or a low pH (or light as discussed below, or light and low pH, etc.). The low pH (or light, or light and low pH, etc.) Initiates (e.g., increases the rate of) the irreversible reaction to produce the diazonium species and the cyclic guanidine species. As previously discussed, the diazonium species may be visually distinct from the triazabutadiene molecule; therefore the reaction produces a visually detectable molecule.

b. Reductive Cleavage

Other mechanisms may be used to break down triazabutadiene molecules of the present invention. For example, in some embodiments, reducing conditions increase the rate at which the triazabutadiene molecules break down. Thus, the present invention also features methods of reductive cleavage of triazabutadiene molecules. For example, triazabutadiene molecules (e.g., triazabutadiene scaffolds) may be readily cleaved using reducing agents such as but not limited to sodium dithionite (sodium hydrosulfite) ($Na_2S_2O_4$). In some embodiments, the reducing agent comprises lithium aluminum hydride, sodium borohydride, or the like. In some embodiments, electrochemical reduction may be used in accordance with the present invention.

Figure 3:
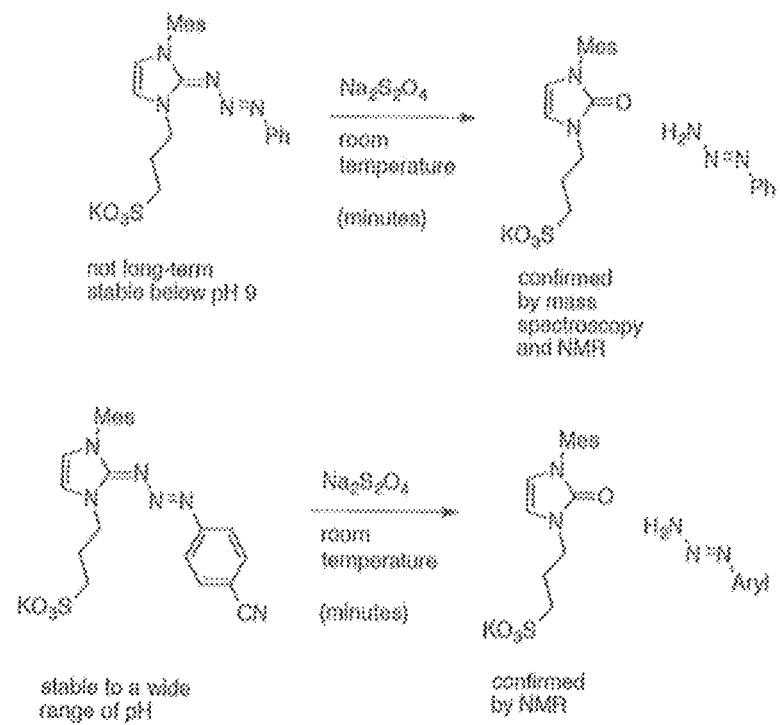
FIG. 3 shows reductive cleavage of triazabutadiene molecules.

Reductive cleavage of the triazabutadiene molecules provides a urea functionality and a terminal aryl triazene (see FIG. 3). In some embodiments, the aryl triazene is further reduced in the presence of excess reducing agent (e.g., sodium dithionite). In some embodiments, the reduction can be observed visually by the change in color of a solution. For example, there may be a subtle change of yellows that results from a loss of a shoulder in UV/vis spectrum.

In some embodiments, the ratio of the concentration of the triazabutadiene to the reducing agent is about 1:1. In some embodiments, the ratio of the concentration of the triazabutadiene to the reducing agent is about 1:2. The present invention is not limited to the aforementioned ratios. For example, in some embodiments, the ratio of the concentration of the triazabutadiene to the reducing agent is about 2:3, 4:5, etc. The present invention is not limited to the aforementioned ratio of concentrations.

In some embodiments, the reduction can occur within about 10 minutes, within about 15 minutes, within about 20 minutes, within about 25 min, within about 30 min, etc., at room temperature.

Without wishing to limit the present invention to any theory or mechanism, it is believed that reductive cleavage of the triazabutadiene molecules is advantageous because it can occur rapidly (e.g., within 10 minutes, within 15 minutes). Also, the triazabutadiene molecules that are highly stable in acid (e.g., a p-CN derived triazabutadiene) may still be susceptible to reducing conditions.

In some embodiments, reductive cleavage of triazabutadiene molecules may also be used to cleave unreacted triazabutadienes that did not undergo diazonium formation/reaction chemistry that is associated with a drop in pH (or other mechanism) as described above (a sort of quench for the pH chemistry).

c. Light-Initiated Cleavage

Figure 4A:
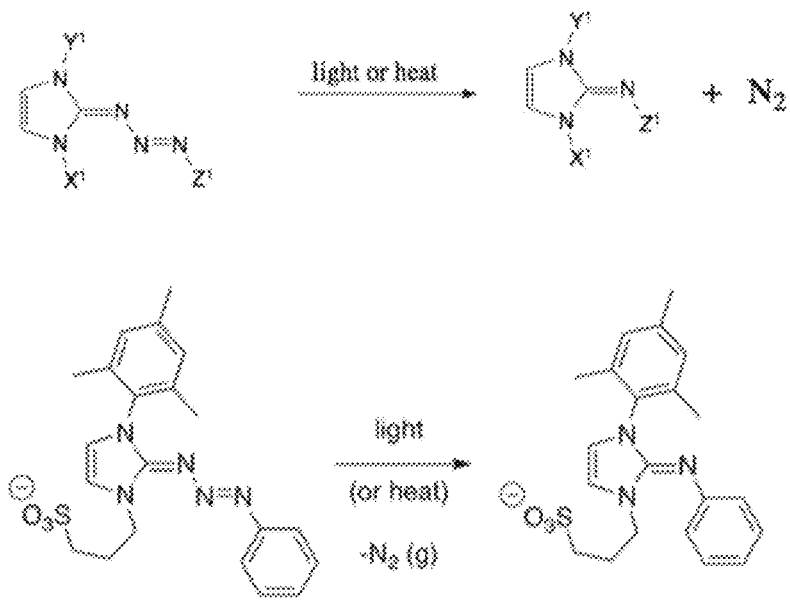
FIG. 4A shows light catalyzed cleavage of triazabutadiene molecules.

Other factors (e.g., in addition to low pH, in addition to reducing conditions) may also enhance or increase the rate of the breakdown of the triazabutadiene molecules. For example, in some embodiments, light increases the rate at which the triazabutadiene molecule breaks down (into the cyclic guanidine species and the diazonium species) (see FIG. 4A).

Figure 4B:
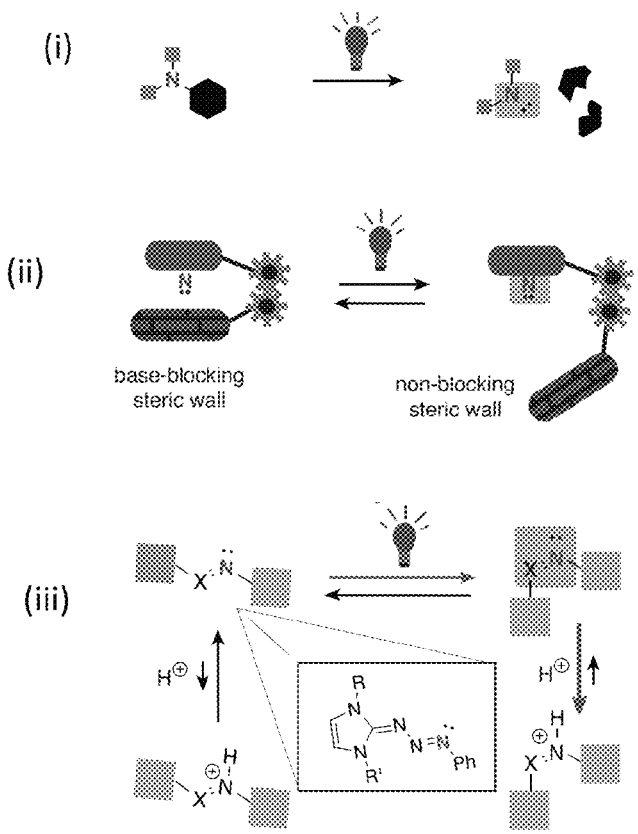
FIG. 4B shows photochemically generated bases. (i) A masked base may decompose to reveal a basic nitrogen atom upon exposure to light; (ii) The basic nitrogen atom of a molecule obscured by a steric wall may be reversibly swung away in a photochemically triggered fashion; (iii) The intrinsic basicity of a nitrogen-containing functional group may be altered by a photochemical event.

The present invention features triazabutadienes that, upon photo-irradiation, may be rendered more basic in a reversible fashion. Referring to FIG. 4B, for reference, a protecting group of a masked base may decompose to reveal a basic nitrogen atom upon exposure to light. Or, a basic nitrogen atom of a molecule obscured by a steric wall may be reversibly swung away in a photochemically-triggered manner. The present invention shows the intrinsic basicity of a nitrogen-containing functional group may be altered by a photochemical event.

In some embodiments, triazabutadiene molecules of the present invention may readily photoisomerize to a more reactive Z-form. An aqueous solution of Compound A was irradiated with a simple hand-held UV lamp ("365 nm," measured at 350 nm). Consumption of Compound A was observed after only a few hours. The non-irradiated reaction under similar conditions was stable for days as partial degradation rapidly renders the solution mildly basic. Without wishing to limit the present invention to any theory or mechanism, it was hypothesized that if a two-electron process were happening, then Compound A-Z would be more basic than Compound A-E. A 1.0 N NaOH solution of Compound A was treated with light. At pH 14, Compound A was stable for weeks in the dark; it was surprisingly discovered that near complete consumption of starting material after 20 hours of constant irradiation occurred.

Figure 4C:
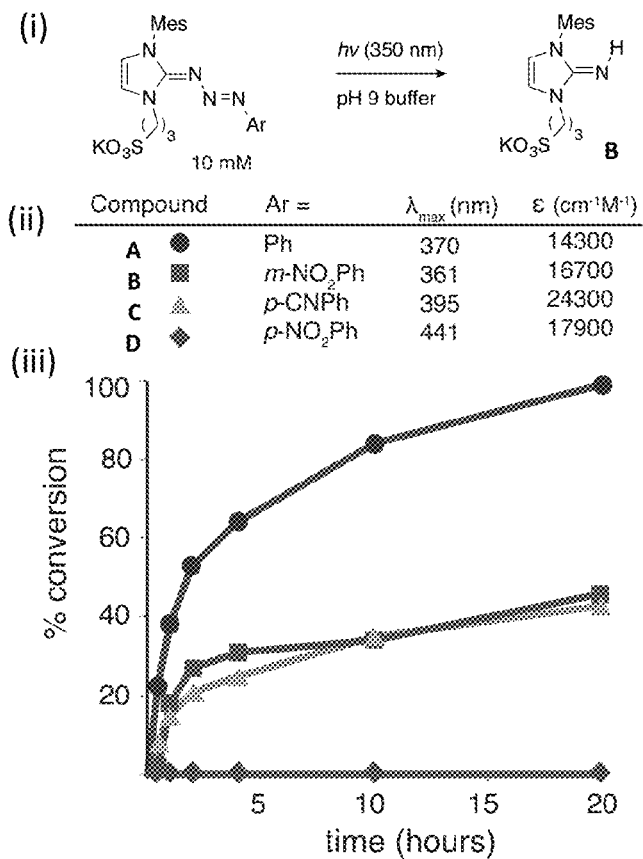
FIG. 4C shows time-dependent photo-induced degradation of triazabutadienes. (i) The reaction was monitored by comparing starting materials (Compounds A-E) with product (Compound B); (ii) Peak absorption and extinction coefficients for all of the compounds were excitable by the UV source used; (iii) Time-dependent conversion of compounds was measured by NMR integration.

Referring to FIG. 4C, NMR analysis of samples post-irradiation showed cyclic guanidine Compound B. Evidence of a benzene diazonium species or phenol/azobenzene products derived therefrom was not observed. Benzene diazonium ions also absorb UV light to expel nitrogen and generate a benzene radical. In order to resolve if the initial cleavage undergoes a radical homolytic mechanism versus a two-electron heterolytic mechanism, a trapping experiment using resorcinol was conducted. (Resorcinol was chosen because it can serve a dual role as a radical scavenger and a trap benzene diazonium species that could be formed.) An excess of resorcinol was added to a pH 9 borate-buffered solution of Compound A and the mixture was irradiated with light. The known azobenzene, Sudan Orange G, was formed in a 65% yield (versus 4% for the non-irradiated reaction).

Derivatives of Compound A were made to examine the effects of electronic perturbations on the light-induced degradation. Electron deficient aryl rings are more stable at lower pH, and this trend generally holds true for the photochemical reactions as well. A buffered borate solution was chosen due to its alkaline nature and lack of complicating signals in the NMR experiment. Compounds C-E all have absorption spectra that are well within the range of the UV lamp (see FIG. 4C(ii)). Both m-$NO_2$ (Compound C) and p-CN (Compound D) had similar rates of reaction, both slower than Compound A. To rule out other effects associated with possible heating or interactions of the buffer, p-$NO_2$ derivative Compound E was irradiated because of its significantly red-shifted spectrum. Compound E absorbed in a range that was not irradiated with the UV lamp and as such was recalcitrant to degradation (see FIG. 4C(iii)).

As previously discussed, poorly (or non-) buffered aqueous solutions could become more basic as a function of time due to the degradation to Compound B and the aryl diazonium species. Without wishing to limit the present invention to any theory or mechanism, it is believed that the cause of the increase in pH is Compound B, which acts as a base. It was found that reactions slowed and eventually stopped once the pH had risen to around 9. Without wishing to limit the present invention to any theory or mechanism, it was hypothesized that by driving the reaction to completion with light, it would be possible to increase the pH beyond this dark-reaction imposed wall (analogous FIG. 4B(ii)). Using NMR and a pH meter, it was observed that the pH of a solution of Compound A irradiated with UV light rose in a time-dependent manner.

In an effort to examine the rate order for the pH-increasing reaction more carefully, in situ, real-time pH measurements were acquired. Compound A was dissolved in water and the pH of the solution was adjusted to 9 such that it would not form Compound B in the absence of light. Upon exposing the solution to 350 nm light, it was surprisingly discovered that the solution rapidly spiked up to a pH of ~10 over the course of several minutes, and only upon much longer exposure slowly became more basic. This spike was not at all consistent with the model of the pH increase being solely linked to the concentration of Compound B being generated. Moreover, previous NMR studies showed that much more time was required to afford a pH change commensurate with this apparent level of degradation.

Figure 4D:
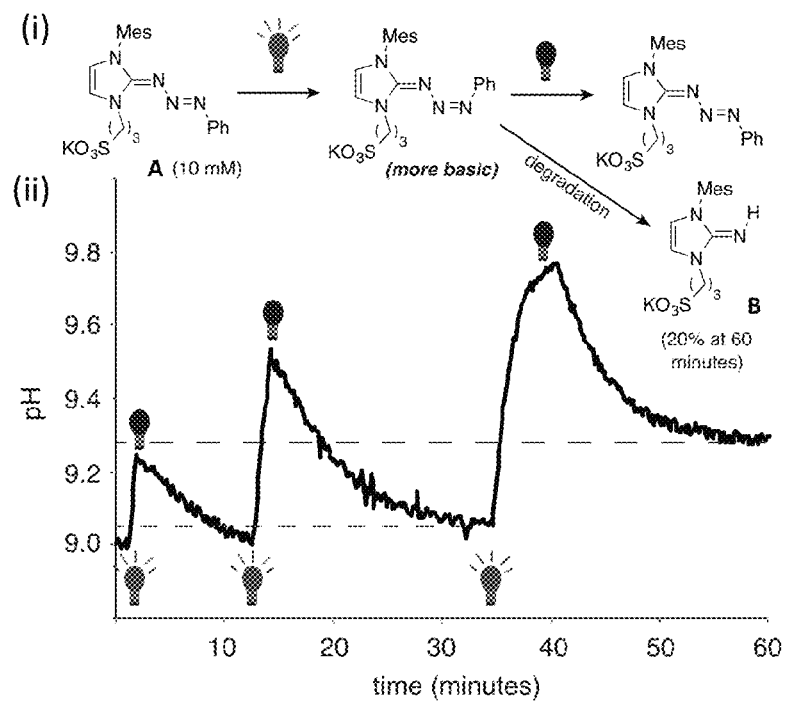
FIG. 4D shows (i) Compound A is rendered more basic upon exposure to light; that basicity recovers (to some extent) in the absence of light; (ii) Oscillating UV irradiation provides a saw-tooth pH trend over time.

Without wishing to limit the present invention to any theory or mechanism, it was hypothesized that the rapid pH increase that was observed was not attributed to Compound B, but instead a result of the Z isomer being significantly more basic than the E isomer (see FIG. 4D(i). A sample was irradiated and then the light was turned off once the pH of the solution started to increase noticeably. As the sample thermally reverted to the more stable E form, the pH of the solution dropped as well (see FIG. 4D(ii)). The experiment was repeated with increasing times of irradiation, and a saw-tooth pattern was obtained. The process was not completely reversible due to some degradation to Compound B. Indeed, triazabutadiene Compound A can serve a dual role of being a photo-masked base (see FIG. 4B(i)), and a base whose intrinsic functional group properties are altered photochemically (FIG. 4B(iii)).

Figure 4E:
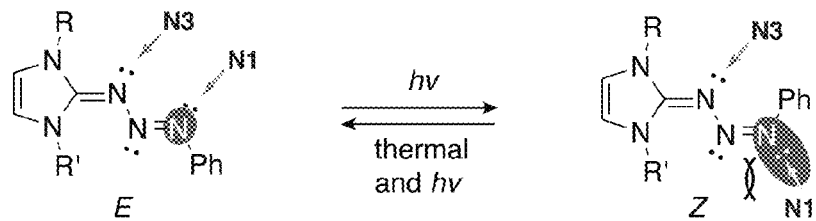
FIG. 4E shows the lone-pair of electrons on the N1 nitrogen atom becomes more electron-rich upon isomerization from E to Z.

Thus, this phenomenon via an isomerization-induced $pK_b$ change was surprisingly discovered by the inventor. Without wishing to limit the present invention to any theory or mechanism, unlike the case where Hecht's compound is rendered basic upon irradiation by way of moving of a steric wall (see FIG. 4B(ii), it is unlikely that steric factors play a significant role in this chemistry, especially in water. It is possible that the E-isomer has alternating "non-π involved" lone pairs of electrons, whereas the Z-isomer has two adjacent "non-π involved" lone pairs of electrons (see FIG. 4E). The electronic repulsion from these renders N1 much more electron rich in Z-isomer and thus a stronger Lewis base.

Referring to FIG. 4C(iii), Compound C and Compound D were examined in an effort to find a base that was reversibly basic but also more resistant to degradation. In both cases, a slow subtle change to the pH was observed, but none as dramatic and rapid as Compound A. Without wishing to limit the present invention to any theory or mechanism, it is believed that this may be due to factors such as (a) faster thermal isomerization to the E isomer such that a build up of the Z isomer is not possible; (b) the electron-deficient triazabutadienes are less basic to begin with, so a transition is not observable in the operating pH range.

It is possible that Compound A may be useful as a photo-catalytic base in the context of organic reactions. With limited solubility in all but DMSO, the stability of Compound A was tested. As noted previously, Compound A is quite stable to an excess of acetic acid in DMSO, showing only 12% degradation over 14 hours at room temperature. Upon irradiation with light, Compound A in presence of acetic acid completely fell apart over the same time frame. To confirm that this was due to the acid, a solution of Compound A (in pure DMSO) was irradiated. After four hours of constant irradiation in acid-free DMSO, an E:Z ratio of nearly 50:50 was observed. Moreover, unlike in water, the thermal reversion from Z to E is slow in pure DMSO with a half-life on the order of days. Attributing this to lack of protonation, a control in MeOD was run, and a first-order thermal isomerization was observed with a rate of $3\times10^{-5}$ s$^{-1}$ ($t_{1/2}$~6.4 hours), in addition to some degradation to Compound B.

Figure 4F:
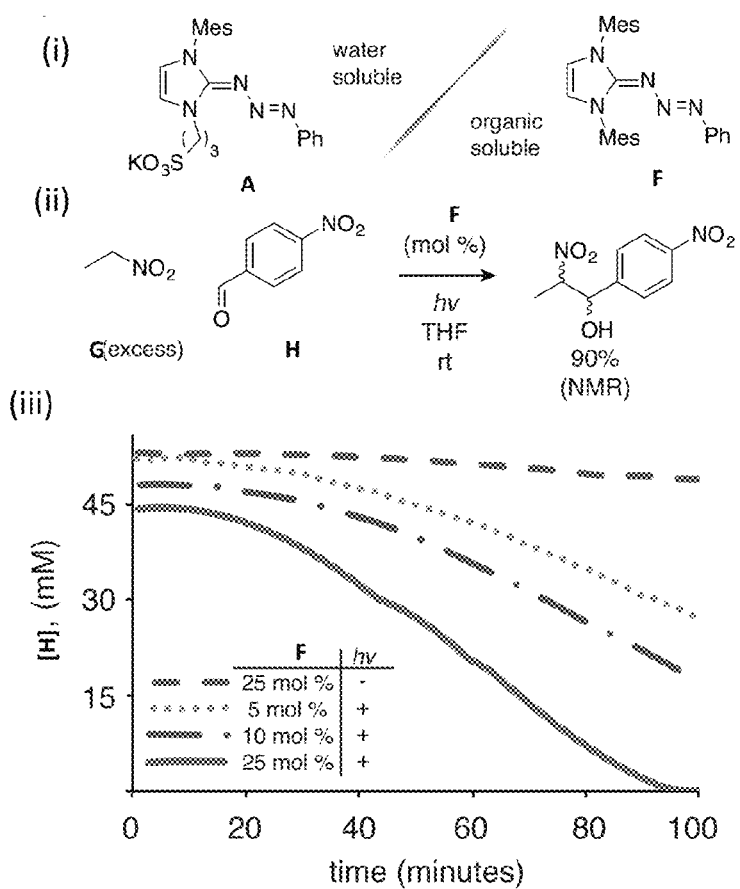
FIG. 4F shows the use of the photobase as a catalyst. (i) Structures of water-soluble Compound A versus organic soluble Compound F; (ii) The Henry reaction between Compound G and Compound H was carried out at room temperature and varying amounts of catalyst; (iii) The reactions were monitored by ReactIR™, following consumption of aldehyde Compound H. Red line=25 mol % Compound F with no light. Orange line=5 mol % Compound F+light. Green line=10 mol % Compound F+light. Blue line=25 mol % Compound F+light.

Due to the limited organic solubility of Compound A, Compound F (FIG. 4F(i)) was synthesized. With Compound F, a similar light-induced acid sensitivity was observed in DMSO (and slow thermal isomerization). Based on the apparent $pK_b$ of Compound F, $pK_a$ were matched to condensation substrates. A Henry reaction between nitroethane (Compound G) and p-nitrobenzaldehyde (H) was chosen to demonstrate the virtues of Compound F (FIG. 4F(ii)). The reaction between Compound G and Compound H occurred rapidly at room temperature in a light and catalyst dependent manner (FIG. 4F(iii)). The reaction with 25 mole % Compound F in the absence of light was exceedingly slow. Likewise, the reaction with light but no catalyst also failed to proceed. The cyclic guanidine was not observed during a post-reaction analysis of the components from a 25 mole % Compound F run, indicating that the Z-isomer of Compound F is likely to be the catalytically active species in solution. Slow thermal isomerization back to the E-isomer in aprotic organic solvents together with a fast overall reaction attempts to adjust the reaction rate prior to consumption of Compound H. Interestingly, the reaction catalyzed with Compound F was significantly faster than the same reaction reported by Hecht. This may provide evidence that Compound F-Z is more basic than Hecht's blocked trialkylamine.

As previously discussed, the present invention features methods of breaking down triazabutadiene molecules by subjecting the molecule to light. The light may, for example, include wavelengths of about 400 nm. The present invention is not limited to wavelengths of 400 nm or about 400 nm. For example, in some embodiments, the wavelength is from 350 nm to 400 nm (e.g., 370 nm). In some embodiments, the wavelength is from 360 nm to 410 nm. In some embodiments, the wavelength is from 330 nm to 420 nm. In some embodiments, the wavelength is from 340 nm to 430 nm.

In some embodiments, the method comprises subjecting the molecule to a low pH and to light.

As previously discussed, light-promoted reactivity and light-facilitating E/Z isomerization has been observed. In some embodiments, a system such as a UV-LED pen may be used for these reactions, however the present invention is not limited to a UV-LED pen and may utilize any appropriate system. The UV-LED pens may allow for relatively narrow bandwidth irradiation of these compounds (but are not limited to these bandwidths). The color of the bulk material shifts as a result of electronic perturbations to the aryl azide starting material. For example, nitro derivative Compound 6e (see FIG. 6D) is rust-red, versus an orange phenyl (Compound 6c, FIG. 6C) and yellow-orange methoxy (Compound 6d, FIG. 6D). It may be possible for selective irradiation of a complex mixture in an orthogonal sense. These experiments may be performed in basic aqueous solutions to maintain the solvation properties of water while also preventing the degradation pathway stemming from protonation. These experiments are not limited to basic aqueous solutions.

III. Synthesis of Triazabutadiene Molecules and Experimental Examples

Synthesis of 1-mesityl-1-H-imidazole: To a solution of 2,4,6-trimethylaniline (1.35 g, 10.0 mmol) in methanol (15 mL) was added a solution of glyoxal (40%) (1.14 mL, 40% in water, 10. mmol). The mixture was stirred at room temperature until a solid formed. Thereafter, solid ammonium chloride (1.07 g, 20 mmol), formaldehyde (37%) (1.6 mL 37% in water, 60. mmol) and methanol (40 mL) were added, and the mixture was heated to reflux for one hour. After the hour, phosphoric acid (1.4 ml of an 85% solution) was added drop wise and the mixture was refluxed for an additional eight hours. Upon cooling to room temperature ice (30 g) was added and the solution was brought to a pH of 9 with potassium hydroxide (40% in water). The following mixture was extracted repeatedly with diethyl ether. The ether phase was dried over magnesium sulfate and solvent removed in vacuo to form a brown solid which was filtered and washed with hexanes to give the product (0.785 g; 42%).

1H NMR (500 MHz, CDCl3): δ 7.45 (t, J=1.1 Hz, 1H), 7.25 (t, J=1.1 Hz, 1H), 6.99 (dp, J=1.3, 0.7 Hz, 2H), 6.91 (t, J=1.3 Hz, 1H), 2.36 (t, J=0.7 Hz, 3H), 2.01 (t, J=0.6 Hz, 6H). 13C NMR (126 MHz, CDCl3) δ 138.80, 137.47, 135.42, 133.40, 129.55, 128.96, 120.02, 21.03, 17.33. (see Liu, J. et al. Synthesis 2003, 17, 2661-2666).

Synthesis of 3-(1-mesityl-1H-imidazol-3-ium-3-yl) propane-1-sulfonate (see FIG. 6F): To a solution of 1-mesityl-1-H-imidazole (1.00 g, 5.36 mmol) in toluene (30 mL) was added 1,3-propanesultone (1.00 g, 8.18 mmol) and the mixture was heated to reflux overnight. The mixture was allowed to cool to room temperature and the off-white precipitate collected by filtration. The precipitate was further washed with diethyl ether and dried using a vacuum oven to yield a solid (1.40 g; 84%). 1H NMR (500 MHz, D2O): δ 8.92 (t, J=1.6 Hz, 1H), 7.75 (t, J=1.8 Hz, 1H), 7.49 (t, J=1.8 Hz, 1H), 7.06 (q, J=0.8 Hz, 2H), 4.44 (t, J=7.1 Hz, 2H), 2.39-2.31 (m, 2H), 2.25 (s, 3H), 1.96 (s, 6H). 13C NMR (126 MHz, D2O) δ 141.42, 136.54, 134.64, 130.74, 124.34, 123.00, 48.18, 47.17, 25.03, 20.17, 16.29.

Synthesis of Potassium 3-(3-mesityl-2-(phenyltriaz-2-en-1-ylidene)-2, 3-dihydro-1H-imidazol-1-yl) propane-1-sulfonate (see FIG. 6G): To a slurry of 3-(1-mesityl-1H-imidazol-3-ium-3-yl)propane-1-sulfonate (50 mg, 0.16 mmol) in dry THF (6 mL), was added a solution of phenyl azide in THF (0.16 mL, 1 M, 0.16 mmol). To the solution was added KO-t-Bu (24 mg, 0.21 mmol) in one portion and the resulting mixture was stirred under argon for 4 hours. Hexanes (1 mL) was then added and the reaction mixture was filtered. The solvent was removed and the residue taken up in a minimal amount of DCM and on trituration with hexanes, pure product was obtained by filtration as a yellow powder (61 mg, 81%). 1H NMR (500 MHz, DMSO-d6) δ 7.32 (d, J=2.4 Hz, 1H), 7.07-7.02 (m, 4H), 6.99-6.94 (m, 1H), 6.84 (d, J=2.4 Hz, 1H), 6.51-6.47 (m, 2H), 4.09 (t, J=7.1 Hz, 2H), 2.34 (s, 3H), 2.12-2.04 (m, 2H), 1.95 (s, 6H). 13C NMR (126 MHz, DMSO-d6) δ 152.19, 151.13, 137.94, 136.15, 134.31, 129.31, 128.60, 125.26, 120.90, 117.61, 117.24, 48.52, 45.05, 25.80, 21.06, 17.95.

Using the procedures described herein, the p-methoxy and p-nitro analogs (from the p-MeO aryl azide and p-NO2 aryl azide) were also prepared.

Figure 9:
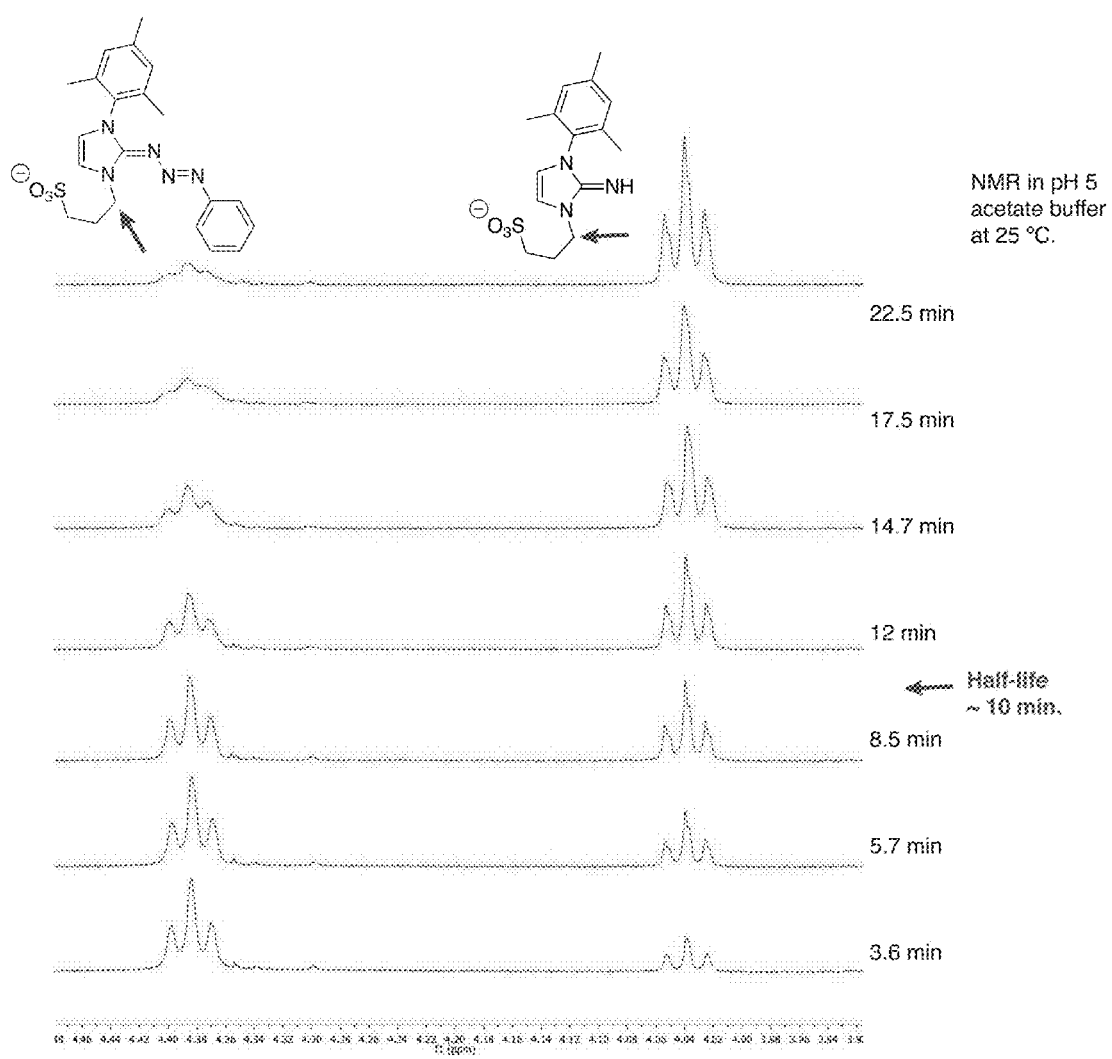
FIG. 9 shows NMR in pH 5 acetate buffer at 25 degrees C.

For decomposition experiments, buffers were made to the appropriate pH in a 9:1 mix of H2O:D2O. These solutions were added to the compound being assayed such that the buffer capacity was at least 10 fold the concentration of the compound. Some experiments used 5 mg compound in 0.5 mL of buffer. These were immediately inserted into an NMR instrument and scans were taken at even time intervals to calculate the half-life of the compound based on integration. FIG. 9 shows an example of NMR in pH 5 acetate buffer at 25 degrees C.

Figure 6A:
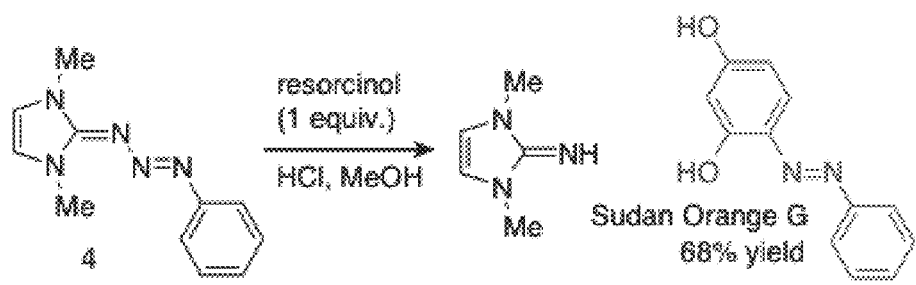

As another non-limiting example, an azide to NHC route may be used to synthesize triazabutadiene molecules (e.g., see FIG. 6H). For example, a triazabutadiene molecule was synthesized from dimethyl imidazole derived NHC and phenyl azide (see Compound 4 in FIG. 6A). Referring to FIG. 6A, when the triazabutadiene molecule (Compound 4) was treated with methanolic HCL, a rapid color change occurred. This change was confirmed to coincide with diazonium formation by trapping the reactive species with resorcinol to provide known diazo dye Sudan Orange G. When the triazabutadiene molecule (Compound 4) was treated with the much less acidic acetic acid, the same product was obtained. Compound 4 was not water-soluble.

Figure 6B:
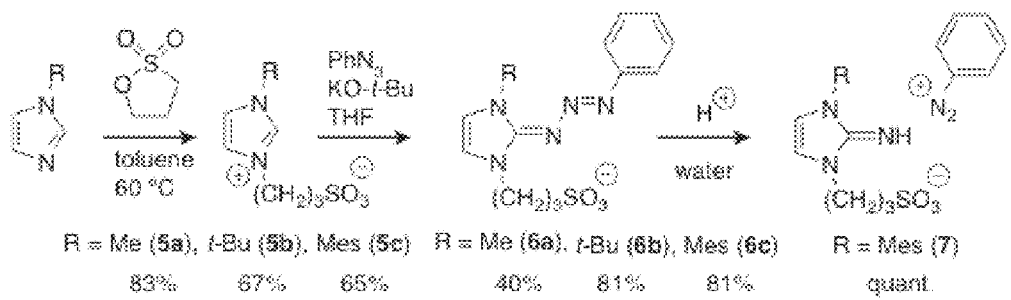

To render the triazabutadiene water-soluble, methyl imidazole was alkylated with propane sultone to provide the Zwitterionic NHC precursor Compound 5a (see FIG. 6B). Formation of the NHC under basic conditions in the presence of phenyl azide yielded the highly water soluble Compound 6a (see FIG. 6B). Compound 6a is highly colored, so its pH dependence was studied using UV/Vis. The reactions were not only pH-, but also scan-frequency dependent. Upon finding this, the stability of Compound 6a was studied in D2O in the dark using NMR. Even in the dark it was unstable, but not in the diazonium-forming way. Both Compound 6b and a more hindered mesityl (Mes) substituted Compound 6c (see FIG. 6B) were synthesized to stabilize what was initially considered to be a rearrangement pathway that could be blocked by steric repulsion. Compound 6c was the most stable of the three (less than 10% consumed after 24 hours versus 50% for Compound 6a and Compound 6b). It is not yet dear that the hypothesis of a simple rearrangement was correct. Dissolution in 0.1 N NaOH rendered all compounds stable (no detectable degradation after 24 hours in the dark).

As mentioned above, Compound 6c was reasonably stable in pure D2O. Upon adjusting the pH to 5 with HCl, a rapid initial consumption of Compound 6c to Compound 7 (see FIG. 6B) and a benzenediazonium salt was noted. After this initial burst of reactivity, a slowing and apparent arresting of the reaction was noted. At this pH the hydronium was the limiting reagent. All future reactions were run in buffers with a buffer capacity sufficient to maintain a large excess of hydronium ions. The experiments were performed in 90:10 H2O:D2O buffered solutions to minimize considerations of pH vs. pD. The decomposition to diazonium salts and Compound 7 was measured as a function of pH in phosphate/citrate buffers from pH 4-7 and in a phosphate buffer from pH 6-8. All runs provided linear correlations of concentration and time, indicating a pseudo-zero order reaction (first order with respect to hydronium ion with a large excess of hydronium ions). While the peaks for Compound 7 remained constant, the peaks associated with Compound 6c drifted downfield as the reaction progressed. This drifting was highly reproducible across samples and buffers, but the underlying cause is not understood at this time. A sigmoidal correlation between rate and buffer pH centered at pH 6 was obtained. When resorcinol was not added to consume the diazonium species, 4-phenylazophenol (Compound 8) was observed (see FIG. 6c). Compound 8 came from the decomposition of one diazonium ion to phenol followed by reaction with a second diazonium ion. The instability of Compound 6c in a pH 7 phosphate buffer was surprising given the stability in D2O. Compound 6c was tested in a non-buffered 90:10 H2O:D2O solution and observed only >7% after 6 hours.

Figure 6C:
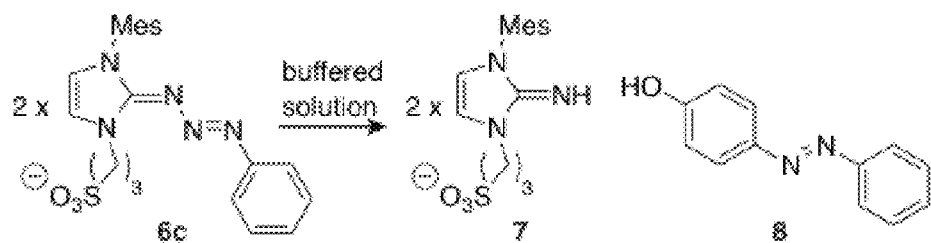
Figure 6D:
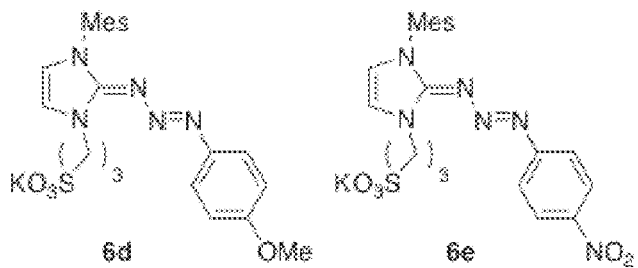

To further examine the reactivity of this class of compounds, variants Compound 6d and Compound 6e were synthesized (see FIG. 6c). It was hypothesized that the p-methoxy and p-nitro analogs (Compound 6d and Compound 6e, respectively) would display different reactivity profiles. It was observed that in pure D2O, 26% of Compound 6d was consumed after 24 hours in the dark at room temperature as compared with Compound 6e, which was stable to within the detection limit of NMR. Preliminary data shows that Compound 6d undergoes decomposition to the diazonium species more rapidly than Compound 6c in pH 5, 6, and 7 phosphate/citrate buffer (rates of 2.0×10−5, 1.0×10−5, and 0.53×10−5 M/s, respectively). Upon attempting the same study with Compound 6e it rapidly precipitated out of solution across the same pH range. After collecting the precipitate and dissolving it in deuterated methanol, no change was observed from a sample of Compound 6e that had never been exposed to a buffered solution. Treatment of this methanolic Compound 6e with HCl led to an immediate color change and diazonium formation was confirmed by trapping with resorcinol. It is possible that 1) the sodium salt of Compound 6e is much less soluble than the potassium salt; or 2) with different solvating ions present the sulfonate interacts with the electron-poor N2 nitrogen atom of the triazabutadiene to break conjugation and form an insoluble complex (this is backed by a reversible color change of the starting rust-red solid, to the light yellow precipitate). Note that the p-nitrobenzenediazonium salts are reported to have the best labeling efficiency of tyrosine residues on proteins.

The influence of solvated ions on reactivity will be studied. In water, or a heavy water/water mixture, a near-zero rate of diazonium salt formation was observed, yet in solutions buffered to pH 7 and even pH 7.4 an increase in the reaction rate was observed. It is possible that the ions in solution are somehow coordinating and facilitating the reaction. This could be a result of the anionic species or the cationic metal. To assess the role of the anionic component, the reaction in the presence of a range of buffers while holding the pH constant will be observed. Buffers that will be evaluated include but are not limited to those expected to have the most diverse properties, e.g., MES, a Zwitterionic morpholino sulfonic acid, and imidazolium chloride, the conjugate acid of a mild base, can both buffer a solution at pH 6.5, but ionic species in solution would be dramatically different. The metals in solution could well be acting as Lewis acids to activate our molecule. A range of metal halide salts dissolved in pure water at varying concentrations will be screened.

Figure 6E:
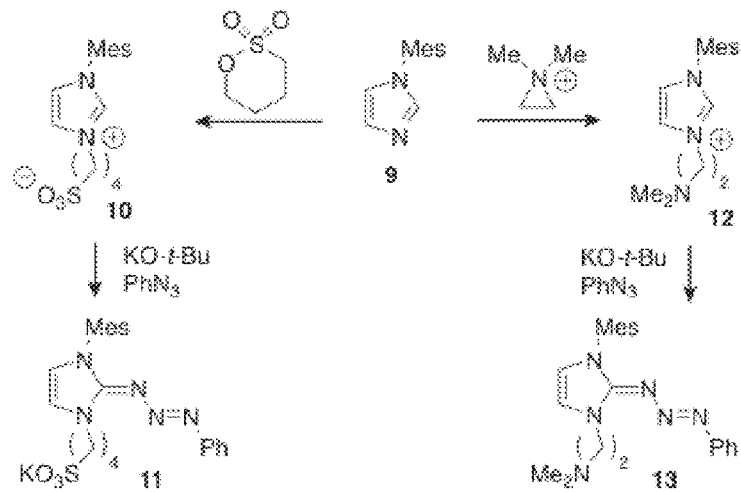

Note that all of the compounds in the 6 series (FIG. 6B, FIG. 6C, and FIG. 6D) have a built-in sulfonate to confer solubility. It is possible that this functional group could be serving an important role by effecting the localization of metals, directing them to interact with the nitrogen atoms of the triazabutadiene and thus alter the reactivity of the compound. This may be happening with Compound 6e to such an extreme that the compound is no longer soluble. This concept of a directed metal binding on triazabutadienes was observed, albeit in an organic environment. To study the role of the side chain, the imidazole core will be alkylated (see Compound 9 of FIG. 6E) with either butane sultone to provide imidazolium (Compound 10 of FIG. 6E) and triazabutadiene (Compound 11 of FIG. 6E), or a dialkyl aziridinium salt to provide the analogous Compound 12 and Compound 13 (see FIG. 6E) which invert the expected charge on the side-chain. The extra methylene in Compound 11 as compared with Compound 6 may alter the way that the side-chain bites back on the triazabutadiene. The tertiary amine will be protonated at physiological pH and as serve to invert the charge of the side arm. Without wishing to limit the present invention to any theory or mechanism, a potential bonus of Compound 13 is that the basic nitrogen may help localize this compound in the most acidic subcellular compartments much like LysoTracker™ dyes.

Regarding the role of mesityl group in reactivity, it is possible that a function of the mesityl in triazabutadiene reactivity is to provide a steric wall to prevent side reactions. It is not yet clear the extent to which the desymmetrization of the imidazole half affects the properties of the triazabutadienes. The NMR of Compound 6c (FIG. 6C) shows a tale of two hydrogen atoms on the imidazole ring. Without wishing to limit the present invention to any theory or mechanism, it is believed that because the ortho methyl groups prevent coplanar aryl rings, the mesityl group is unlikely to sit in conjugation with the imidazole, but the highly differentiated chemical environments might be explained by: 1) the mesityl u-system deshielding the adjacent hydrogen atom, and 2) the aryl ring having an inductive effect. Changing the p-methyl of the mesityl to electron donating and withdrawing groups may allow the adjustment of the electronic parameters without disrupting the steric bulk.

Figure 7A:
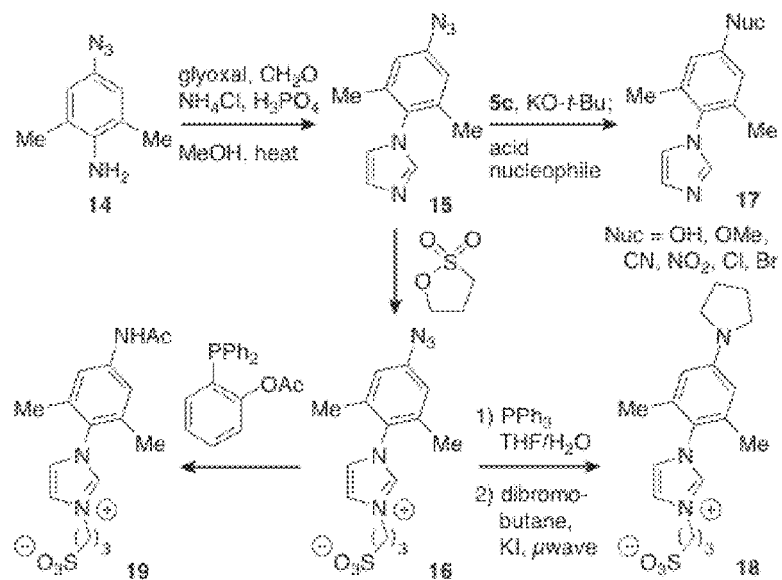
FIGS. 7A, 7B, 7C, and 7D show non-limiting examples of triazabutadienes.

Synthesis may be performed as shown below with known p-azido dimethyl aniline (Compound 14, see FIG. 7A) because it may lead to a wide range of substituted compounds. From imidazole (Compound 15, FIG. 7A) one can alkylate with 1,3-propanesultone to provide NHC precursor Compound 16 (FIG. 7A), or prior to that one can treat with an NHC to access the wealth of diazonium chemistry to provide Compound 17 (FIG. 7A) in all of its forms. Solvolysis in water or alcoholic solvent may provide a phenol or aryl ether, and copper mediated Sandmeyer-type chemistry may afford cyano, nitro or halogenated aryl species. From imidazolium Compound 16 Staudinger chemistry followed by aniline alkylation may provide Compound 18 (FIG. 7A), or traceless Staudinger-Bertozzi ligation may yield Compound 19 (FIG. 7A). These substrates cover a range of Hammett values while also providing an additional site of attachment to proteins, fluorophores, surfaces, etc.

Figure 7B:
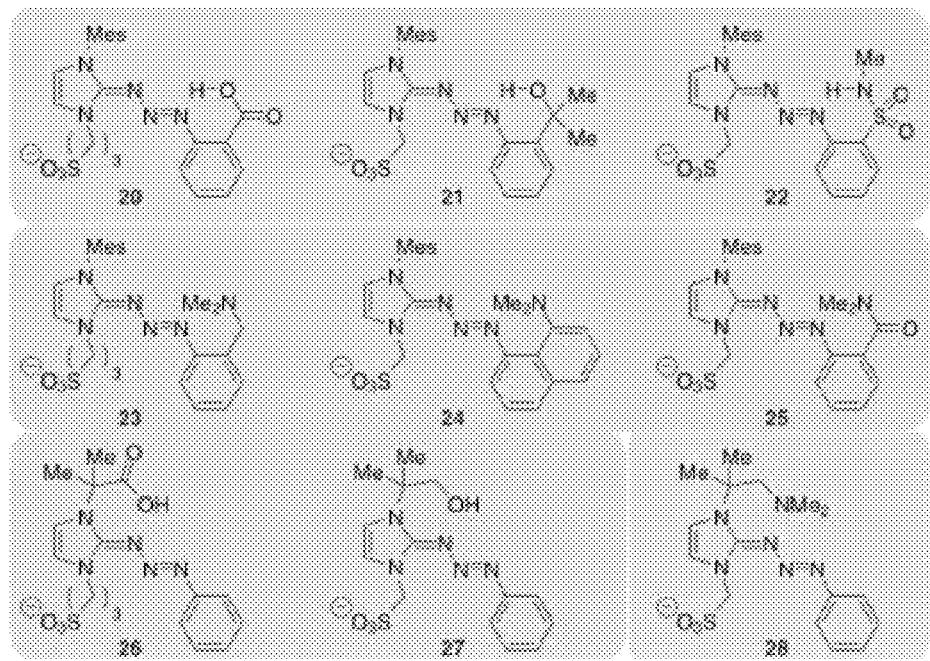

Regarding the role of intramolecular hydrogen bond acceptors/donors in reactivity, it may be possible to synthesize a series of triazabutadienes with hydrogen bond donors that possess a range of pKa values (Compounds 20-22, see FIG. 7B). In addition to H-bond donors, it may be possible to synthesize a series of internal bases (Compounds 23-25, see FIG. 7B). It may be possible that amine bases (e.g., dimethyl amine) positioned near the N1 nitrogen will favor protonation at N3 and thus make the triazabutadiene less stable to acidic media. These compounds are all synthetic targets given a strategy of coupling with aryl azides. The delicate triazabutadiene functional group is installed last under mild conditions.

Figure 7C:
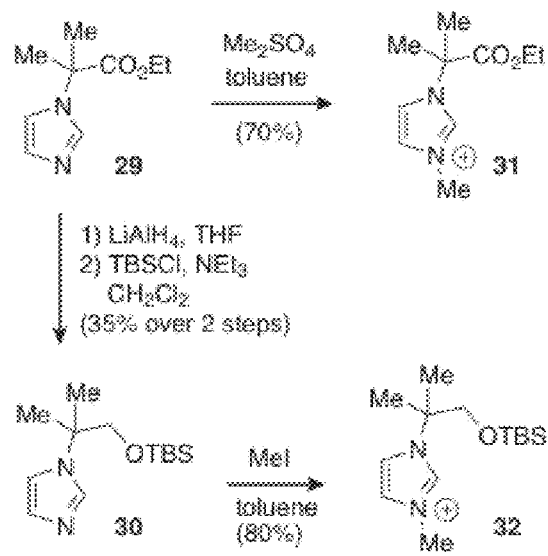

In addition to compounds that are designed to activate/deactivate the N1 nitrogen, it may be possible to synthesize a series of compounds where the N3 nitrogen in most likely to be affected (Compounds 26-28, FIG. 7B). An NHC with a hydrogen bond donor on a short arm was made. As in FIG. 7C, the synthesis of Compounds 26-28 from known Compound 29 may start with either alkylation to a compound like Compound 31 or reduction and protection to compound 30 followed by alkylation to Compound 32. If the mesityl is absolutely essential for a desired reactivity profile, a H-bond donor/acceptor may be inserted on a methyl group in the ortho position of the mesityl ring.

Figure 7D:
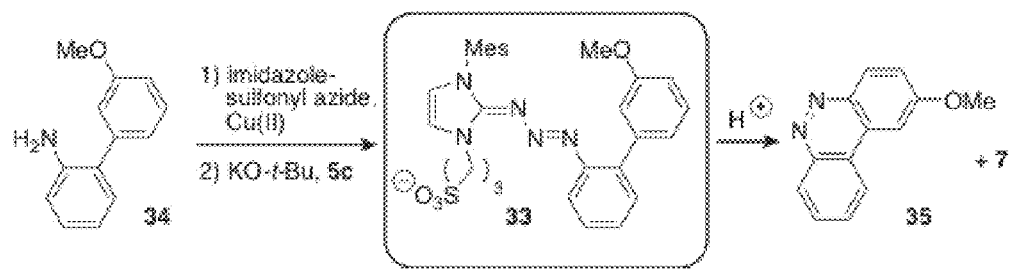

Regarding intramolecular trapping of diazonium species, it may be possible to synthesize triazabutadienes with adjacent functional groups that will rapidly consume the diazonium species. For example, Compound 33 (see FIG. 7D) contains an aryl ring, positioned ortho to the masked diazonium. The synthesis may start from a diazo transfer reaction to convert aniline Compound 34 (FIG. 7D) to an aryl azide. Coupling with Compound 5c (FIG. 6B) may complete the synthesis. It is possible that following diazonium unmasking an aromatic substitution reaction will occur to provide benzocinnoline Compound 35 (FIG. 7D). Because this reaction is intramolecular one might be able to use a non-activated ring, rendering the ring electron rich. The methyl ether may serve as a site of attachment to chemical cargos. A second type of intramolecular diazonium trap that could be employed is a beta keto ester that is also ortho to the diazonium produced. Beta keto esters are known to react with diazonium species through enol form, and can generate oxo-cinnolines, which are biologically active cores.

IV. Applications and Methods of Use

The triazabutadiene molecules of the present invention may be utilized for a variety of purposes.

Figure 8:
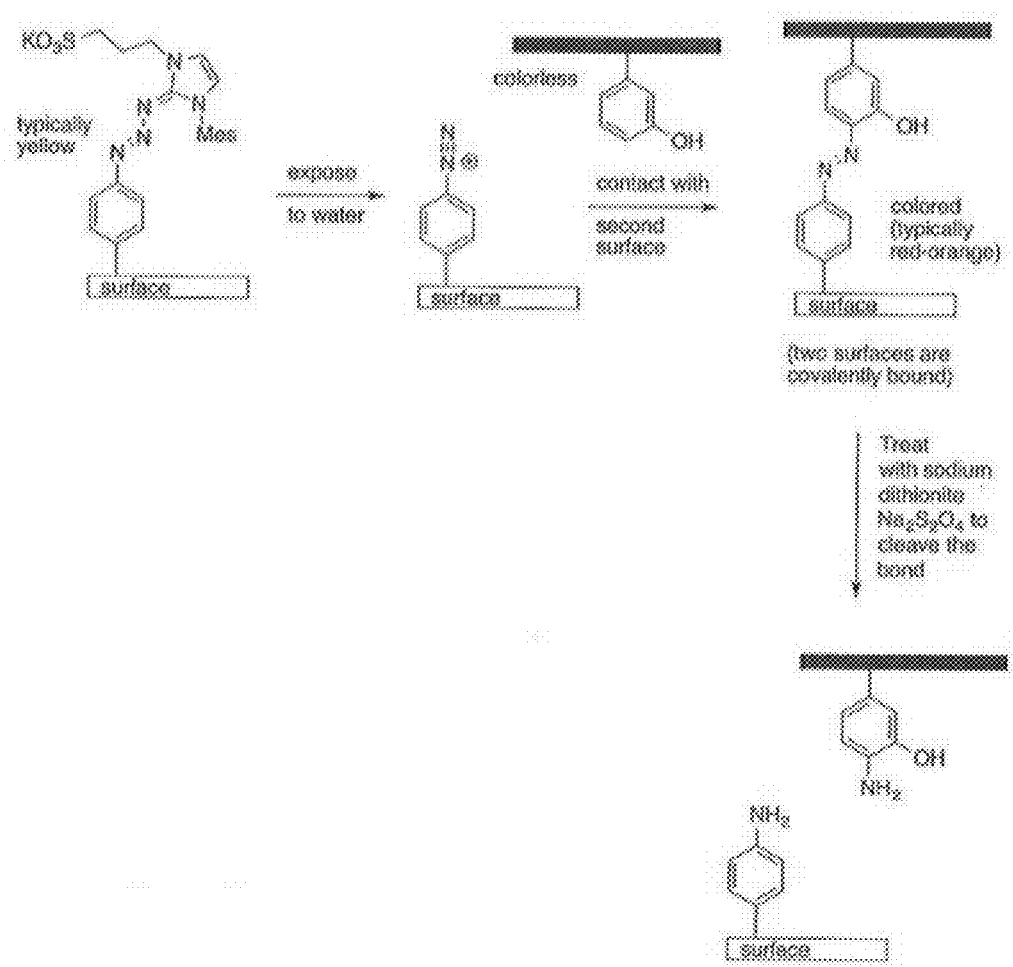
FIG. 8 shows an example of triazabutadiene molecules used as adhesives.

As previously discussed, the present invention features triazabutadienes as adhesives. FIG. 8 shows a triazabutadiene molecule bonded to a first surface. A phenol-containing compound is bonded to a second surface. First and/or second surfaces may include but are not limited to glass, plastic, a biomaterial, or any other appropriate surface, e.g., a surface that allows for linkage chemistry, e.g., the first surface could be any surface that allows for the attachment of a triazabutadiene molecule, the second surface could be any surface that allows for the attachment of a phenol-containing compound. Non-limiting examples of materials also include Tufnol materials such as phenolic cotton laminated plastics, phenolic paper laminated plastics, etc., a phenol formaldehyde resin such as bakelite (or baekelite), etc. As in FIG. 8, the first reaction (wherein the triazabutadiene molecule is exposed to water to result in diazonium species formation) may be performed at room temperature; however, the reaction may be at a different temperature, e.g., depending on the environmental conditions. Without wishing to limit the present invention to any theory or mechanism, it is believed that different temperatures may affect the rate at which the first reaction (wherein the triazabutadiene molecule is exposed to water to result in diazonium species formation) and/or the second reaction (wherein the diazonium species reacts with the phenol-containing compound on the second surface) occurs. FIG. 8 also shows cleavage of the azobenzene linkage upon treatment with the reducing agent sodium dithionite. In some embodiments, the reducing agent is not sodium dithionite but is another appropriate reducing agent. In some embodiments, the surface (e.g., glass, plastic, etc.) is modified, e.g., using an etching mechanism. In some embodiments, photolithography etching may be used to shape the available triazabutadiene molecules. For example, one may intentionally expose certain triazabutadiene molecules to light (e.g., in a pattern via a mask, for example) so as to transition them to the diazonium species; if left unreacted, the diazonium species will then transition to a phenolic compound (as previously described), and thus will be non-sticky or unreactive with the phenol-containing compound on a second surface. This system can allow for the etching away of undesired triazabutadienes.

As previously discussed, the present invention features triazabutadienes as additives in adhesive systems. In some embodiments, triazabutadienes are used with (e.g., added to) adhesives systems such as existing adhesive systems (e.g., epoxy adhesive systems). Epoxy adhesive systems typically comprise an epoxy compound (epoxy resin) and a co-reactant (curing agent or hardener), wherein the adhesive is formed when the co-reactant reacts with the epoxy compound. The present invention features formulations comprising a triazabutadiene and an epoxy compound, wherein the formulation is adapted to react with a curing agent (co-reactant) to form an adhesive. Epoxy resins and curing agents are well known to one of ordinary skill in the art. Examples of epoxy resins include but are not limited to bisphenol A epoxy resins and glycidylamine epoxy resins. Examples of curing agents include but are not limited to amines and thiols. Note that the triazabutadiene can be attached to either the amine or epoxy side. Similarly, the electron-rich aryl (e.g., phenol) can similarly be added to either component (or both).

Figure 10A:
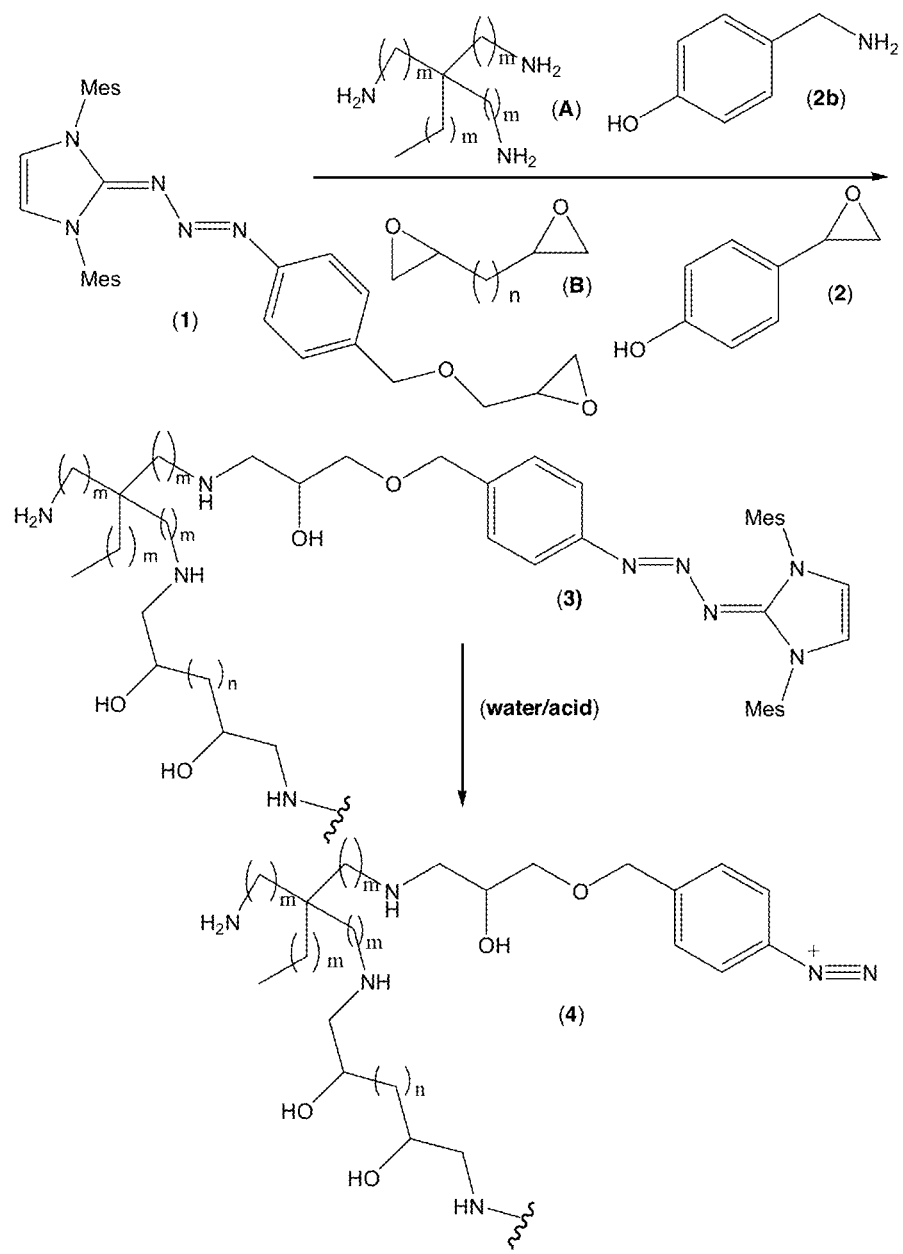
FIG. 10A shows an example of a triazabutadiene comprising an epoxide (Compound 1) that can be added to an epoxy resin (Compound B).

In some embodiments, the triazabutadiene comprises an epoxide (e.g., epoxide or other appropriate epoxy group). A non-limiting example of a triazabutadiene comprising an epoxide is shown as Compound 1 in FIG. 10A. The epoxide triazabutadiene may be mixed with an epoxy residue (Compound B in FIG. 10A), e.g., to generate a formulation. Note that the present invention is not limited to the epoxy residue shown in FIG. 10A. In some embodiments, the formulation (formulation comprising the triazabutadiene and the epoxy resin) further comprises an electron-rich aryl ring group (e.g., phenol or other appropriate group) with an epoxide (see Compound 2). This may help provide additional electron rich aryl rings (e.g., phenol groups) with which the aryl diazonium species can react (subsequent to subjecting the triazabutadiene to appropriate conditions so as to yield said aryl diazonium species). Also shown in FIG. 10A is a non-limiting example of a co-reactant (curing agent). In some embodiments, an electron-rich aryl ring (e.g., phenol group) (see Compound 2b) is added to the co-reactant. As previously discussed, this may help provide additional electron rich aryl rings (e.g., phenol groups) with which the aryl diazonium species can react.

The reaction of the formulation (Compound 1 and Compound B; or Compound 1, Compound 2, and Compound B) and the co-reactant (Compound A; or Compound A and Compound 2b) yields Compound 3, e.g., a polymerized triazabutadiene. Exposure of Compound 3 to water (or other appropriate conditions such as acid) yields the aryl diazonium species (e.g., Compound 4). Compound 4 is available for reacting with electron-rich aryl rings, which can provide for the adhesive properties.

Figure 10C:
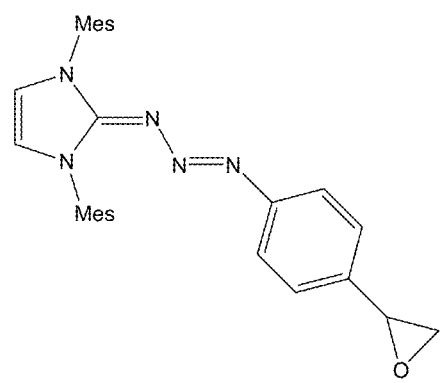
FIG. 10C shows an example of an alternative epoxide triazabutadiene.
Figure 11:
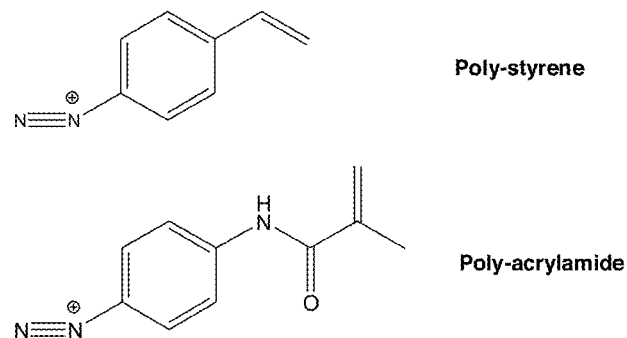
FIG. 11 shows polystyrene (as if attached to the $N_3$ area of a triazabutadiene, e.g., in lieu of an epoxide as shown in Compound 1 of FIG. 10A) and polyacrylamide (as if attached to the $N_3$ area of a triazabutadiene, e.g., in lieu of an epoxide as shown in Compound 1 of FIG. 10A). Other classes of polymers may be contemplated in lieu of epoxide, polyacrylamide, polystyrene, etc.

The present invention is not limited to triazabutadienes comprising an epoxide. For example, in some embodiments, the triazabutadiene any appropriate class of polymer (e.g., for polymerization processes), e.g., polystyrene, α-β-unsaturated ester acrylate, or the like. The class of polymer may be one that does not require heat for polymerization (or does not require heat such that the triazabutadiene functionalities would be compromised or destroyed). For reference, FIG. 11 shows polystyrene as if attached to the $N_3$ area of a triazabutadiene, e.g., in lieu of an epoxide as shown in Compound 1 of FIG. 10A. FIG. 11 also shows polyacrylamide as if attached to the $N_3$ area of a triazabutadiene, e.g., in lieu of an epoxide as shown in Compound 1 of FIG. 10A. In some embodiments, the triazabutadiene comprises an amine. In some embodiments, the triazabutadiene has a structure similar to that of FIG. 10C, wherein the triazabutadiene is shortened relative to Compound 1 of FIG. 10A (the epoxide is directly linked to the aryl ring). In some embodiments, the triazabutadiene is an azide-containing compound that can be clicked onto other compounds as desired.

The formulation may comprise any appropriate percentage of triazabutadiene. For example, the formulation may comprise a particular percentage of triazabutadiene that provides desired properties (e.g., cure time, cure strength, color, melting/decomposition temperature, ability to heal (e.g., allow for initially unreacted triazabutadiene molecules to yield the diazonium species which subsequently bond to nearby phenol-containing compounds) of the adhesive or polymer.

In some embodiments, the formulation comprises from 0.01% to 0.1% triazabutadiene. In some embodiments, the formulation comprises from 0.01% to 1% triazabutadiene. In some embodiments, the formulation comprises from 0.01% to 10% triazabutadiene. In some embodiments, the formulation comprises from 0.01% to 20% triazabutadiene. In some embodiments, the formulation comprises from 0.1% to 1% triazabutadiene. In some embodiments, the formulation comprises from 0.1% to 10% triazabutadiene. In some embodiments, the formulation comprises from 0.1% to 20% triazabutadiene. In some embodiments, the formulation comprises from 0.1% to 30% triazabutadiene. In some embodiments, the formulation comprises from 0.1% to 40% triazabutadiene. In some embodiments, the formulation comprises from 0.1% to 50% triazabutadiene. In some embodiments, the formulation comprises from 1% to 10% triazabutadiene. In some embodiments, the formulation comprises from 1% to 20% triazabutadiene. In some embodiments, the formulation comprises from 1% to 30% triazabutadiene. In some embodiments, the formulation comprises from 1% to 40% triazabutadiene. In some embodiments, the formulation comprises from 1% to 50% triazabutadiene. In some embodiments, the formulation comprises from 1% to 60% triazabutadiene. In some embodiments, the formulation comprises from 1% to 70% triazabutadiene. In some embodiments, the formulation comprises from 1% to 80% triazabutadiene. In some embodiments, the formulation comprises from 1% to 90% triazabutadiene. In some embodiments, the formulation comprises between 10% to 20% triazabutadiene. In some embodiments, the formulation comprises between 20% to 30% triazabutadiene. In some embodiments, the formulation comprises between 30% to 40% triazabutadiene. In some embodiments, the formulation comprises between 40% to more than 50% triazabutadiene.

In some embodiments, the formulation comprises about 0.01% triazabutadiene. In some embodiments, the formulation comprises about 0.1% triazabutadiene. In some embodiments, the formulation comprises about 0.5% triazabutadiene. In some embodiments, the formulation comprises about 1% triazabutadiene. In some embodiments, the formulation comprises about 2% triazabutadiene. In some embodiments, the formulation comprises about 5% triazabutadiene. In some embodiments, the formulation comprises about 10% triazabutadiene. In some embodiments, the formulation comprises about 15% triazabutadiene. In some embodiments, the formulation comprises about 20% triazabutadiene. In some embodiments, the formulation comprises about 25% triazabutadiene. In some embodiments, the formulation comprises about 30% triazabutadiene. In some embodiments, the formulation comprises about 40% triazabutadiene. In some embodiments, the formulation comprises about 50% triazabutadiene. In some embodiments, the formulation comprises more than about 50% triazabutadiene. The present invention is not limited to the aforementioned percentages.

In some embodiments, the reaction of the triazabutadiene molecule to the diazonium species occurs in water within 10 seconds. In some embodiments, the reaction of the triazabutadiene molecule to the diazonium species occurs in water within 30 seconds. In some embodiments, the reaction of the triazabutadiene molecule to the diazonium species occurs in water within 1 minute. In some embodiments, the reaction of the triazabutadiene molecule to the diazonium species occurs in water within 5 minutes. In some embodiments, the reaction of the triazabutadiene molecule to the diazonium species occurs in water within 10 minutes. In some embodiments, the reaction of the triazabutadiene molecule to the diazonium species occurs in water within 15 minutes. In some embodiments, the reaction of the triazabutadiene molecule to the diazonium species occurs in water within 20 minutes. In some embodiments, the reaction of the triazabutadiene molecule to the diazonium species occurs in water within 25 minutes. In some embodiments, the reaction of the triazabutadiene molecule to the diazonium species occurs in water within 30 minutes. In some embodiments, the reaction of the triazabutadiene molecule to the diazonium species occurs in water within 45 minutes. In some embodiments, the reaction of the triazabutadiene molecule to the diazonium species occurs in water within 60 minutes.

In some embodiments, the bonding of the diazonium species to the phenol-containing compound occurs within 10 seconds. In some embodiments, the bonding of the diazonium species to the phenol-containing compound occurs within 30 seconds. In some embodiments, the bonding of the diazonium species to the phenol-containing compound occurs within 1 minute. In some embodiments, the bonding of the diazonium species to the phenol-containing compound occurs within 5 minutes. In some embodiments, the bonding of the diazonium species to the phenol-containing compound occurs within 10 minutes. In some embodiments, the bonding of the diazonium species to the phenol-containing compound occurs within 15 minutes. In some embodiments, the bonding of the diazonium species to the phenol-containing compound occurs within 20 minutes. In some embodiments, the bonding of the diazonium species to the phenol-containing compound occurs within 25 minutes. In some embodiments, the bonding of the diazonium species to the phenol-containing compound occurs within 30 minutes. In some embodiments, the bonding of the diazonium species to the phenol-containing compound occurs within 45 minutes. In some embodiments, the bonding of the diazonium species to the phenol-containing compound occurs within 60 minutes.

In some embodiments, light can be used to speed up the reaction. In some embodiments, varying triazabutadienes amounts can be added to speed up or slow down the reaction. In some embodiments, a surplus of triazabutadienes may be used, which may help allow for an amount of triazabutadiene molecules that are unreacted (and those unreacted triazabutadienes may be buried amongst other reacted compounds). These unreacted triazabutadienes that are buried may be useful in the event of a break in the seal. For example, a break in the seal may cause water to then react with the unreacted triazabutadiene molecules to yield the diazonium species, and those newly formed diazonium species can then subsequently bond to nearby phenol-containing compounds to perhaps "heal" the break in the seal or strengthen the bond.

The present invention also features systems (or kits) comprising said formulations, e.g., kits comprising a triazabutadiene (e.g., triazabutadiene comprising an epoxide) and an epoxy resin. In some embodiments, the kit further comprises a co-reactant (or a formulation with a co-reactant and an electron-rich aryl ring compound), wherein the formulation is adapted to react with the co-reactant to form an adhesive.

Figure 10B:
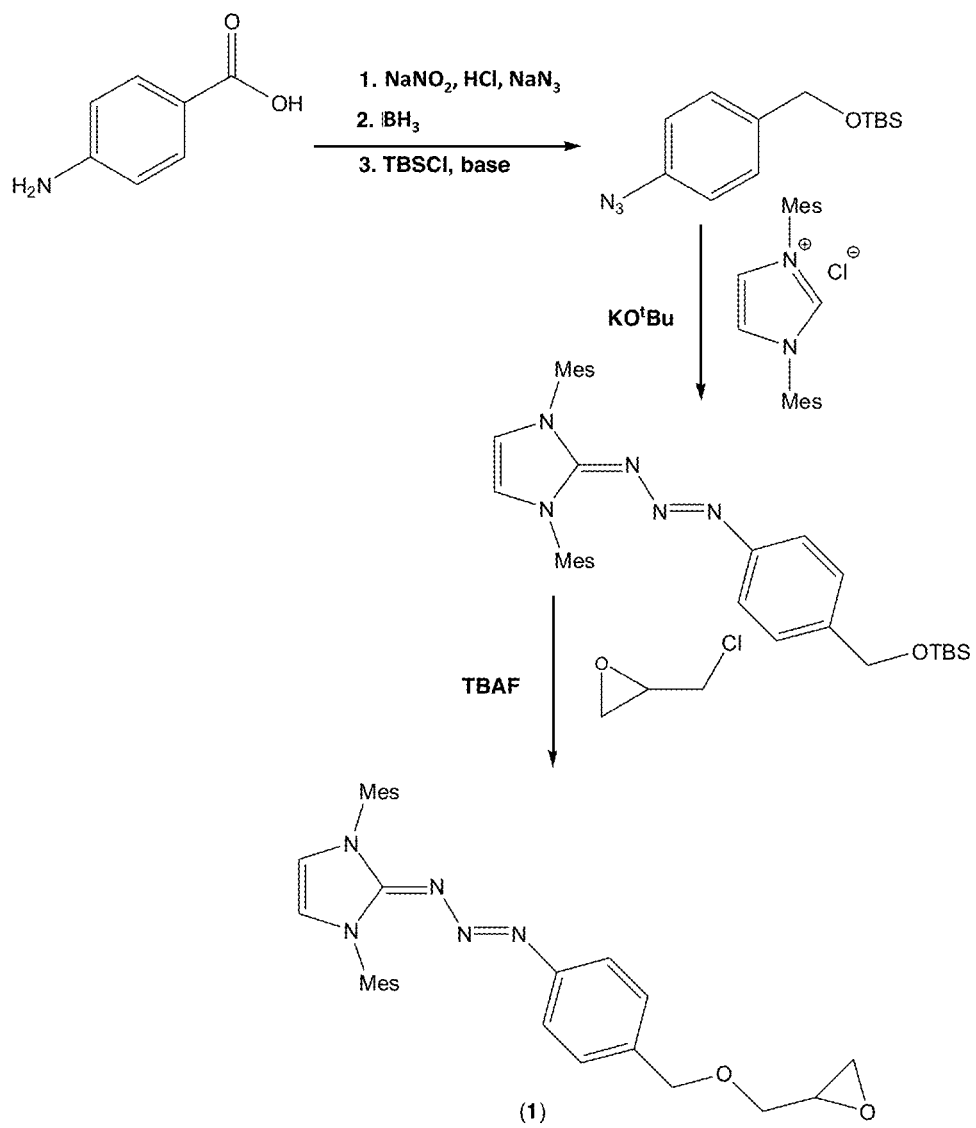
FIG. 10B shows an example of synthesis of a triazabutadiene (Compound 1) comprising an epoxide.

Triazabutadienes for use as additives to adhesive or polymerization systems may be synthesized in a variety of ways. FIG. 10B shows a non-limiting example of synthesis of a triazabutadiene (Compound 1 from FIG. 10A) comprising an epoxide. For example, in some embodiments, aryl azides that are appropriately functionalized (e.g., with an epoxide or functional group that can be converted to an alkyl azide) may be coupled with N-heterocyclic carbenes to form the triazabutadiene core. The present invention is not limited to the compound or step shown in FIG. 10B. For example, in some embodiments, TBS-Cl (tert-butyldimethylsilyl chloride) may be optional. In some embodiments, an alternative to epoxide is added to the triazabutadiene in lieu of epoxide.

As previously discussed, the covalent bond formed between the phenol-containing compound and the diazonium compound forms a colored compound. In some embodiments, the color is red, orange, or a mix of red and orange. In some embodiments, the formation of the color can be used as a positive indicator that the bonding reaction has occurred.

As previously discussed, the diazonium species, if not reacted with the phenol-containing compound, can break down into a phenolic compound (e.g., the diazonium species will extrude nitrogen gas to generate an aryl cation that will rapidly be quenched by solvating water, thus generating the phenolic compound). This reaction is typically much slower than the second reaction (wherein the diazonium species reacts with the phenol-containing compound bound to the second surface). This phenomenon can allow for the unreacted diazonium species to eventually become non-sticky, or unreactive, which may be beneficial in certain circumstances (e.g., photolithography).

Thus, without wishing to limit the present invention to any theory or mechanism, it is believed that the system and methods of the present invention are advantageous because the technology provides underwater adhesion, the adhesive bond may be colored (e.g., highly colored azobenzene linkages), which may serve as a positive indicator that the desired reaction has occurred; and/or the chemical compounds (e.g., unreacted diazonium species) may degrade over time so that the unbonded surface does not remain sticky (e.g., adapted for adhesion) permanently.

In some embodiments, triazabutadienes of the present invention are used as after-market adhesives, e.g., formulations for application to any appropriate surface. For example, the triazabutadienes may be coated on one side of a surface and then activated (e.g., with water) to activate adhesive properties.

In some embodiments, the triazabutadienes are used as or are used in combination with bio-adhesives (e.g., natural underwater adhesives such as mussel adhesive proteins).

As previously discussed, the present invention features triazabutadienes that can cross-react with existing chemistries, e.g., epoxy chemistry), e.g., an epoxide-containing compound, an amine containing compound, an azide-containing compound that can be clicked onto other compounds as required. As an example of synthesis, aryl azides that have been appropriately functionalized (e.g., with an epoxide or functional group that can be converted to an alkyl azide) may be coupled with N-heterocyclic carbenes to form the triazabutadiene core. The present invention is not limited to this route.

As previously discussed, the properties of the formulations featuring the triazabutadiene compounds (e.g., triazabutadiene compounds with the epoxy resins or the like) may be assessed. For example, in some embodiments, gel time/cure time is assessed (e.g., assessing if it is longer, shorter, or similar as compared to samples prepared in the absence of the triazabutadiene additive). In some embodiments, cure strength is assessed (e.g., via break-strength). For example, small (e.g., 0.5×2×5 cm) molded ingots may be broken; strength may be compared to samples prepared in the absence of the triazabutadiene additive. In some embodiments, the color of the material (e.g., the final material) is assessed, e.g., color changes may be observed. In some embodiments, odor is assessed (e.g., is there a strong odor, is there a change in odor). In some embodiments, viscosity is assessed, e.g., as compared to samples prepared in the absence of the triazabutadiene additive. In some embodiments, melting/decomposition temperature is assessed, e.g., via testing in a melt-temp apparatus. In some embodiments, healing potential is assessed, e.g., ability to enhance adhesive bonding (if broken) using water. For example, in some embodiments, ingots may be cracked and submerged into water (and broken faces pushed together) and then be subjected to break-strength test.

The disclosures of the following documents are incorporated in their entirety by reference herein: U.S. Pat. No. 8,617,827; U.S. Pat. Application No. 2009/0048222; U.S. Pat. No. 3,591,575. U.S. Pat. No. 3,607,542; U.S. Pat. No. 4,107,353; WO Pat. No. 2008090554; U.S. Pat. No. 4,218,279; U.S. Pat App. No. 2009/0286308; U.S. Pat. No. 4,356,050; U.S. Pat. No. 8,603,451; U.S. Pat. No. 5,856,373; U.S. Pat. No. 4,602,073; U.S. Pat. No. 3,959,210. The disclosures of the following publications are incorporated in their entirety by reference herein: Kimani and Jewett, 2015, *Angewandte Chemie International Edition* (DOI: 10.1002/anie.201411277—Online ahead of print). Zhong et al., 2014, Nature Nanotechnology 9, 858-866; Stewart et al., 2011, J Polym Sci B Polym Phys 49(11):757-771; Poulsen et al., 2014, Biofouling 30(4):513-23; Stewart, 2011, Appl Microbiol Biotechnol 89(1):27-33; Stewart et al., 2011, Adv Colloid Interface Sci 167(1-2):85-93; Hennebert et al., 2015, Interface Focus 5(1):2014.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A triazabutadiene molecule according to formula 1,

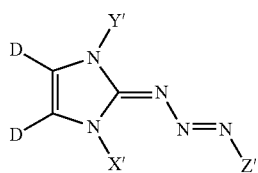

wherein
A=S, O, or N;
D=H, —CH=CH—CH=E-, halides, cyano, sulfonates, alkyl chain, or trifluoromethyl;
E=H, —CH=CH—CH=D-, halides, cyano, sulfonates, alkyl chain, or trifluoromethyl;
$X^l$=—$R^1$-$Q^1$; wherein —$R^1$=alkanes and $Q^1$=sulfonate, phosphate, or a quaternary ammonium cation, or an alkyl, aryl or propargylic containing moiety that can facilitate coupling to other azides via [3+2]cycloaddition chemistry;
$Y^l$=tri-substituted aryl group or alkyl substituents; and
$Z^l$=polymerization residue.

2. The triazabutadiene molecule of claim 1, wherein $R^1$ of $X^l$ comprises $C_{1-6}$ alkylenes.

3. The triazabutadiene molecule of claim 1, wherein the tri-substituted aryl group of Y' comprises a NHS-ester moiety; an oligonucleotide; a peptide; a fluorescence quencher; a pro-fluorophore; an alkyne or a triazene.

4. The triazabutadiene molecule of claim 1, wherein the polymerization residue of $Z^l$ comprises an epoxide.

5. The triazabutadiene molecule of claim 1, wherein the polymerization residue comprises polystyrene, α-β-unsaturated ester acrylate, polyacrylamide, or an amine.

6. A formulation comprising a triazabutadiene molecule and an epoxide resin, the triazabutadiene molecule comprises:

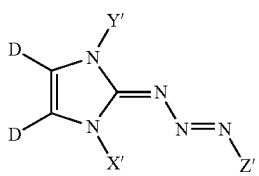

wherein
A=S, O, or N;
D=H, —CH=CH—CH=E-, halides, cyano, sulfonates, alkyl chain, or trifluoromethyl;
E=H, —CH=CH—CH=D-, halides, cyano, sulfonates, alkyl chain, or trifluoromethyl;
$X^l$=—$R^1$-$Q^1$; wherein —$R^1$=alkanes and $Q^1$=sulfonate, phosphate, or a quaternary ammonium cation, or an alkyl, aryl or propargylic containing moiety that can facilitate coupling to other azides via [3+2]cycloaddition chemistry;
$Y^l$=tri-substituted aryl group or alkyl substituents; and
$Z^l$=polymerization residue.

7. The formulation of claim 6, wherein the epoxide resin comprises an aliphatic epoxide.

8. The formulation of claim 7, wherein the aliphatic epoxide comprises:

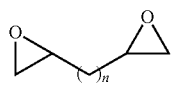

wherein n=1-10.

9. The formulation of claim 6, wherein the epoxide resin comprises an electron rich aryl compound.

10. The formulation of claim 9, wherein the epoxide resin comprises:

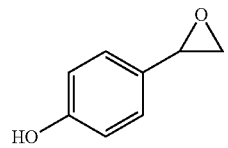

11. A method of producing an adhesive, the method comprises:

a) providing a composition A which comprises:

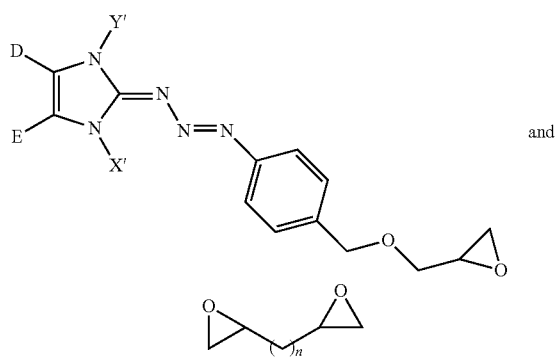

or

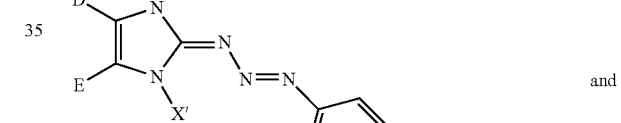

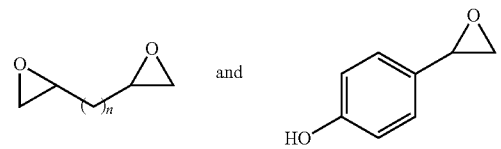

wherein
A=S, O, or N;
D=H, —CH=CH—CH=E-, halides, cyano, sulfonates, alkyl chain, or trifluoromethyl;
E=H, —CH=CH—CH=D-, halides, cyano, sulfonates, alkyl chain, or trifluoromethyl;
$X^l$=—$R^1$-$Q^1$; wherein —$R^1$=alkanes and $Q^1$=sulfonate, phosphate, or a quaternary ammonium cation, or an alkyl, aryl or propargylic containing moiety that can facilitate coupling to other azides via [3+2]cycloaddition chemistry;
$Y^l$=tri-substituted aryl group or alkyl substituents; and
n=1-10;

b) providing a composition B which comprises:

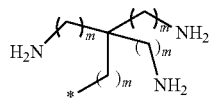

or

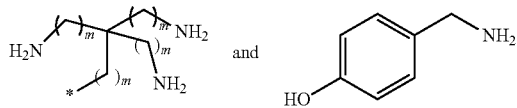 and 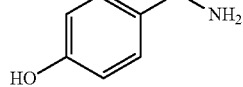

wherein m=1-5; and c) mixing composition A and composition B to form a product C, product C being the adhesive, product C comprises:

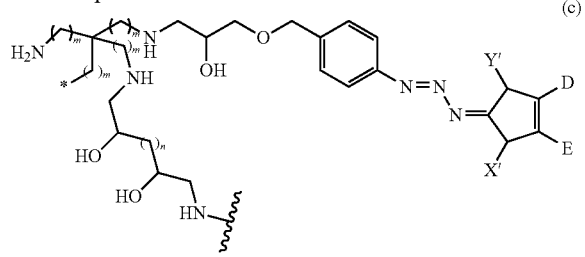

(c)

wherein

A=S, O, or N;

D=H, —CH=CH—CH=E-, halides, cyano, sulfonates, alkyl chain, or trifluoromethyl;

E=H, —CH=CH—CH=D-, halides, cyano, sulfonates, alkyl chain, or trifluoromethyl;

$X^l$=—$R^1$-$Q^1$; wherein —$R^1$=alkanes and $Q^1$=sulfonate, phosphate, or a quaternary ammonium cation, or an alkyl, aryl or propargylic containing moiety that can facilitate coupling to other azides via [3+2]cycloaddition chemistry;

$Y^l$=tri-substituted aryl group or alkyl substituents;

m=1-5; and n=1-10.

12. The method of claim 11, wherein the method further comprises exposing product C to water, whereby a diazonium species is formed from the triazabutadiene, the diazonium species reacts with an electron rich aryl compound.

13. The method of claim 12, wherein the electron rich aryl compound comprises a phenol compound.

\* \* \* \* \*